United States Patent [19]
Ye et al.

[11] Patent Number: 6,013,672
[45] Date of Patent: Jan. 11, 2000

[54] AGONISTS OF METABOTROPIC GLUTAMATE RECEPTORS AND USES THEREOF

[75] Inventors: Zu-Cheng Ye; Harald W. Sontheimer, both of Birmingham, Ala.

[73] Assignee: UAB Research Foundation, Birmingham, Ala.

[ * ] Notice: This patent issued on a continued prosecution application filed under 37 CFR 1.53(d), and is subject to the twenty year patent term provisions of 35 U.S.C. 154(a)(2).

[21] Appl. No.: 08/993,760

[22] Filed: Dec. 18, 1997

[51] Int. Cl.$^7$ .................................................. A61K 31/195
[52] U.S. Cl. ............................................. 514/561; 514/562
[58] Field of Search ...................................... 514/561, 562

[56] References Cited

U.S. PATENT DOCUMENTS 5,622,981  4/1997  Eveleth et al. ............................ 514/380

FOREIGN PATENT DOCUMENTS

WO 9427602   5/1994   WIPO .
WO 94/27602  12/1994  WIPO ............................. A61K 31/42

OTHER PUBLICATIONS

Kaatz et al. Neuroscience (Oxford) 66(1), 55–65 (Abstract).

*Primary Examiner*—Theodore J. Criares
*Attorney, Agent, or Firm*—Benjamin Aaron Adler

[57] ABSTRACT

Astrocytes protect neurons from excitotoxic injury by maintaining low extra-cellular glutamate concentrations ($[Glu]_o$). Compromised astrocytic glutamate uptake has been implicated in acute and chronic neurological conditions, including Parkinson's disease. This invention provides evidence that $[Glu]_o$ is modulated in a feed-back manner through activation of metabotropic glutamate receptors (mGluRs), particularly group II mGluRs. Furthermore, ACPD effects were mimicked by glutamate, suggesting that astrocytic glutamate transport is dynamically regulated with mGluRs acting as sensors for changes in [Glu]. Consequently, agonists of mGluR receptors are potent drugs to modulate extracellular glutamate levels in ways that are neuroprotective.

9 Claims, 34 Drawing Sheets

(A) 0.2 mM MPTP (B) 0.03 mM glutamate

AGONISTS OF METABOTROPIC GLUTAMATE RECEPTORS AND USES THEREOF

FEDERAL FUNDING LEGEND

This invention was produced in part using funds obtained through grant R01 31234 and P50 HD32901 from the National Institutes of Health. Consequently, the federal government has certain rights in this invention.

BACKGROUND OF THE INVENTION

1. Field of the Invention

The present invention relates generally to the field of cell biology and the neurology of neurodegenerate diseases. More specifically, the present invention relates to the manipulation of receptors/transporters that are involved in the uptake/release of glutamate into or out of cells.

2. Description of the Related Art

In the central nervous system, extracellular glutamate concentrations ($[Glu]_o$) are maintained at 1-2 $\mu$M (Benveniste et al. 1984; Nicholls et al., 1990). This is accomplished by a class of recently cloned Na+-dependent transporters (Storck et al. 1992; Pines et al. 1992; Kanai et al., 1992) expressed by neurons and glial cells. Knock-out studies (Rothstein et al. 1996) suggests that the glial transporter, GLT-1, which has the highest affinity for glutamate ($K_m=2$ $\mu$M), is particularly important in controlling $[Glu]_o$.

Intracellular glutamate concentrations ($[Glu]_i$) in astrocytes can readily reach concentrations of several millimolar (Ottersen, 1989; Levi et al., 1992) and thus provide a significant glutamate source in the CNS. Astrocytic glutamate transport can operate in reverse, leading to the non-vesicular release of glutamate (Szatkowski et al. 1990; Attwell et al. 1993), which may contribute to neurotoxic $[Glu]_o$ surges under conditions of energy failure or in conjunction with neurodegenerative diseases (Choi et al., 1990; Ogata et al. 1992). In addition to preventing pathological increases in glutamate, astrocytic glutamate uptake also assures synaptic transmission in the healthy brain. Small increases in the resting $[Glu]_o$ ($\approx$1-2 $\mu$M) would change the activation of many glutamate receptors (Patneau et al., 1990; Forsythe et al., 1990; Izumi et al. 1992; Zorumski et al. 1996) and could have pronounced effect on synaptic transmission.

Modulation of glutamate transporter expression and activity in neurons and glial cells has been studied to some extent (Swanson et al. 1997; Gegelashvili et al., 1997). However, the modulation of astrocytic glutamate transport by $[Glu]_o$ is largely unknown. One candidate receptor class that could serve as $[Glu]_o$ sensors in neurons is the family of metabotropic glutamate receptors (mGluRs). Eight mGluR subtypes have been cloned (Pin et al., 1995) and can be classified according to their amino acid homology, pharmacological profile and signal transduction cascade. Group I receptors (mGluR1, 5) are linked to the phosphoinositol (PI) signaling pathway (Masu et al. 1991; Kawabata et al. 1996); Group II receptors (mGluR 2, 3) and group III receptors (mGluR 4,6,7,8) mediate their effect through changes in cyclic AMP (cAMP) levels (Casabona et al. 1992; Genazzani et al. 1993; Prezeau et al. 1994; Winder et al., 1995; Kemp et al. 1996).

In addition to neurons, glial cells also express mGluR receptors (Tanabe et al. 1993; Miller et al. 1995; Petralia et al. 1996). Immunohistochemical studies suggest that the major glial mGluR receptor is mGluR3 (Tanabe et al. 1993; Testa et al. 1994; Petralia et al. 1996). However, pharmacological studies showed that glial mGluR receptor activation can lead to IP3 mediated calcium release (Masu et al. 1991; Porter et al., 1995) or changes in cAMP levels (Baba et al. 1993; Winder et al. 1996) suggestive of an involvement of Group I and II receptors, respectively. Functional roles for mGluRs in glial cells are just emerging (Winder et al., 1996). Particularly, it has been proposed that glial mGluRs may participate in the communication between neurons and glial cells (Porter et al., 1996; Winder et al. 1996) or may protect neurons from excitotoxic injury (Nicoletti et al. 1996; Bruno et al. 1997).

Parkinson's disease (PD) is a devastating neurological condition that affects a large and growing segment of the aged population. The disease, which affects primarily individuals over age 40, is severely dehabilitating and poses a tremendous societal burden. Clinically, Parkinson's disease presents with tremor, rigidity and deficits in equilibrium and posture. It is now clear that these symptoms result from dysfunction in the basal ganglia, structures consisting of the corpus striatum, globus pallidus and substantia nigra, that receive their major input from motor cortex on which they project back via the thalamus. The principal neurotransmitter used in the nigrostriatal pathway is dopamine.

The presence of large concentrations of dopamine in the striatum was first recognized in the 1950s, and experiments in which dopamine was depleted with reserpine in rats produced symptoms reminiscent of Parkinson's disease. Consistent with these early observations, postmortem basal ganglia from Parkinson's disease patients are severely devoid of dopamine (Hornykiewicz, 1966), suggesting that the symptoms of Parkinson's disease are caused by a dopamine deficiency of the striatum.

The anatomic pathology of Parkinson's disease is well defined, but the pathogenesis remains an enigma. The loss of dopamine-containing neurons in the substantia nigra and the presence of eosinophilic inclusion bodies in these degenerating neurons are the anatomic hallmark of Parkinson's disease, and it is probable that this defined lesion accounts for all it's symptoms.

In the early 1980s, the study of Parkinson's disease received an interesting twist and lead to the first implication of glial cells in the pathogenesis of Parkinsonism. In an effort to produce a "synthetic heroin" not controlled by the FDA, a chemist in California produced 1-methyl-4-phenyl-1-1,2,3,6-tetrahydropyridine (MPTP) as a contaminant. Users of the MPTP contaminated narcotic, within a week of drug use, developed severe and irreversible parkinsonism (Langston et al. 1983). Subsequent controlled administration of MPTP in primates established that MPTP was an exquisitely selective neurotoxin and an excellent animal model of Parkinson's disease became available. The mechanism of action of MPTP is now well understood, and involves its binding to monoamine oxidase (MAO), which converts MPTP to 1-methyl-4-phenylpyridinium ($MPP^+$). $MPP^+$ is avidly and selectively accumulated by the catecholamine uptake system in dopamineric neurons (Snyder et al., 1986). Once taken up it presumably causes cell death by inhibiting mitochondrial oxidation (Nicklas et al. 1985).

Interestingly, the enzyme MOA that converts MPTP to the toxic $MPP^+$ is almost exclusively located in glial cells, particularly in astrocytes (Levitt et al. 1982), and it could be shown experimentally that $MPP^+$ is produced by glial monoamine oxidase (Ransom et al. 1987). In many instances, disease-related neuronal loss (as in Parkinson's disease) is a consequence of neurotoxicity, the uncontrolled build-up of amino acids in toxic concentrations (Choi, 1988a). Glutamate toxicity, in particular, has been implicated in the neuronal loss associated with stoke, epilepsy, and Alzheimer's disease (Choi, 1988a; Choi et al., 1990b; Choi, 1988b). In the healthy brain, neurotoxicity is prevented by highly effective uptake mechanisms that transfer the transmitter from the extracellular space predominantly into astroglial cells (Nicholls et al., 1990; Walz, 1989). Such high-affinity uptake has been demonstrated for glutamate, GABA, aspartate and dopamine (Walz, 1989; Hertz, 1979). Once inside the cell, the transmitter is metabolized or converted into an inactive precursor form. For instance, the glial enzyme glutamine synthetase converts glutamate into glutamine, which is released to serve as neuronal precursor for glutamate biosynthesis (Hertz, 1979). Not only does the build-up or supply of amino acids at neurotoxic concentration result in neuronal lesion, but a failure of glial cells to effectively sequester neurotoxins will have equally devastating consequences. It was recently shown that glial cells may not only fail to sequester transmitter, but may in fact release amino-acids by a reversal of the transport systems that normally functions in the unidirectional uptake of transmitter into the glial cytoplasm (Szatkowski et al. 1990). Interestingly, dopaminergic neurons in the striatum express glutamate transmitter receptors, suggesting that they are susceptible to glutamate toxicity as well (Mereu et al. 1991).

Thus, the prior art is deficient in drugs and methodology to regulate the levels of glutamate in the extracellular space surrounding neuronal and glial cells. The present invention fulfills this long-standing need and desire in the art.

SUMMARY OF THE INVENTION

The present invention demonstrated that mGluRs could serve as sensors that monitor changes in $[Glu]_o$ and may in turn modulate glial glutamate transport. Using primary cultures of postnatal hippocampal astrocytes, it was shown that glutamate, through activation of mGluRs, could induce a long lasting modulation of astrocytic glutamate transport, resulting in enhanced glutamate uptake in concert with attenuation of non-vesicular glutamate release.

Activation of mGluRs, most likely group II in hippocampal astrocytes, exerted a modulatory effect on $Na^+$-dependent glutamate transport. In particular, extracellular glutamate concentration is greatly reduced by mGluR agonists, primarily by a reduction in non-vesicular release accompanied by enhancement of uptake. Astrocytic transport of glutamate is modulated by prior exposure to glutamate itself, which suggest an novel glial-neuronal communication. Astrocytes wrapping active synapse will alter their transport of glutamate and establish a new set point for $[Glu]_o$, thus tuning the responsivity of both presynatic and postsynaptic glutamate receptors.

One object of the present invention is to provide a method of regulating the extracellular glutamate concentration surrounding cells, comprising the steps of contacting said cells with a metabotropic glutamine receptor agonist, whereby the extracellular levels of glutamate are decreased.

In an embodiment of the present invention, there is provided a method of increasing uptake of glutamate into glial cells in an individual in need of such treatment, comprising the step of contacting said cells with a pharmacologically effective dose of a metabotropic glutamate receptor agonist.

In yet another embodiment of the present invention, there is provided a method of treating an individual having a pathophysiological state characterized by an increased level of extracellular glutamate, comprising the step of administering to said individual a therapeutically effective dose of a metabotropic glutamate receptor agonist.

In yet another embodiment of the present invention, there is provided a method for decreasing the level of extracellular glutamate, wherein said agonist is selected from the group consisting of trans-ACPD, 1S3R-ACPD, 1R3S-ACPD, S-4CPG, and L-CCG-I.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should riot be considered to limit the scope of the invention.

FIG. 2 shows that ACPD attenuates extracellular glutamate levels.

FIG. 4 shows that 1S3R-ACPD reduced non-vesicular glutamate release from astrocytes without affecting intracellular glutamate ($[Glu]_i$).

FIG. 5 shows that trans-ACPD or 1S3R-ACPD, but not KA or NMDA, induced a dose-and time-dependent enhancement of glutamate uptake in hippocampal astrocytes cultures. Rate of uptake was determined by $^3$H-D-Asp and normalized to protein content.

FIG. 7 shows that ACPD effects are stereospecific and can be mimicked by other group II mGluRs agonists. Normalized glutamate release was plotted as a function of drug concentrations to yield dose-effect curves.

FIG. 9 shows that manipulation of cAMP levels and inhibition of protein synthesis has no effect on [Glu]$_o$ or ACPD induced reduction in glutamate release.

FIG. 10 shows that glutamate can mimic ACPD-induced effects on [Glu]$_o$.

DETAILED DESCRIPTION OF THE INVENTION

Figure 1:
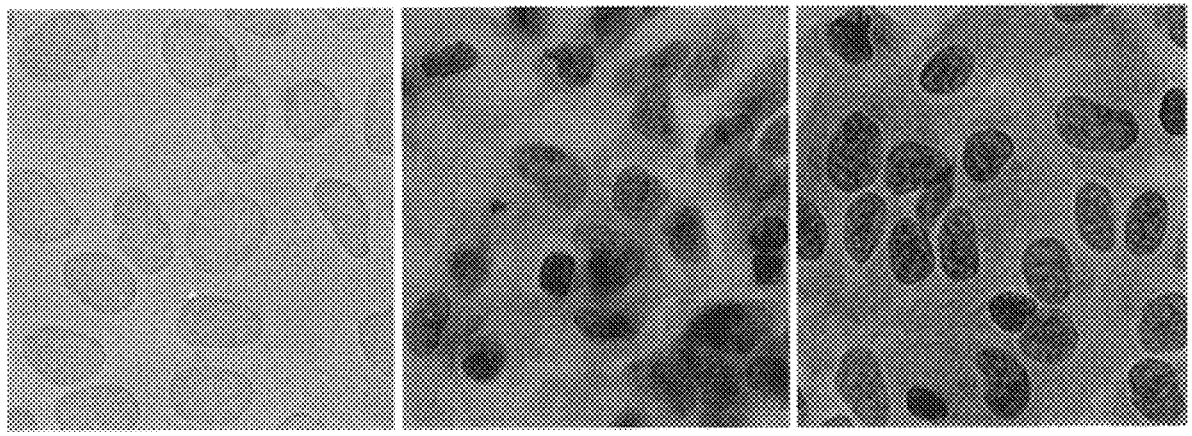
FIG. 1 shows immunohistochemical identification of metabotropic glutamate receptors: Hippocampal astrocyte cultures (8 DIV, P9) were stained with antibodies specific for mGluR1α and mGluR2/3. mGluRs immunoreactivity was visualized by the ABC-DAB method. Astrocytes showed positive staining for both mGluR1α and mGlu2/3. Control cells (no primary antibody) had negative staining (nuclei were stained with hematoxylin).

The present invention is directed towards a method of eliminating toxic levels of glutamate in brain cells, particularly by neuronal and glial cells, wherein a metabotropic glutamate receptor (mGluR) is stimulated with an agonist to increase the uptake of glutamate and decrease the release of glutamate from said cell, whereby this treatment results in nontoxic levels of extracellular glutamate.

As used herein, the abbreviations are as follows: 1S3R-ACPD: (1S,3R)-1-aminocyclopentane-1,3-dicarboxylic acid; 1R3S-ACPD: (1R,3S)-1-aminocyclopentane-1,3-dicarboxylic acid; trans-ACPD: trans-1-aminocyclopentane-1,3-dicarboxylic acid; 1S,3S-ACPD: (1S,3S)-1-aminocyclopentane- 1,3-dicarboxylic acid; (1R, 3S)-1-aminocyclopentane-1,3-dicarboxylic acid, L-AP4: L(+)-2-amino-4-phosphonobutyric acid; L-CCG-I: (2S,3S,4S)-2-(carboxycyclopropyl) glycine or (2S,1'S,2'S)-2-(carboxycyclopropyl) glycine; L-CSA: L-cystein-sulfinic acid; S-4CPG: (S)-4-carboxyphenylglycine; DHPG: (S)-3,5-dihydroxyphenylglycine; PDC: 1-trans-pyrrolidine-2,4,-dicarboxylate; THA: DL-threo-β-hydroxyaspartate.

The present invention is directed to a method of increasing uptake of glutamate into glial cells in an individual in need of such treatment, comprising the step of contacting said cells with a pharmacologically effective dose of a metabotropic glutamate receptor agonist. Desirably, such a treatment results in a reduction in neuronal extracellular levels of glutamate. In general, a person having average skill in this area of research would recognize, given the teachings disclosed herein, that any metabotropic glutamate receptor agonist could have specific therapeutic value. Representative examples of such metabotropic glutamate receptor agonists include trans-1-aminocyclopentane-1,3-dicarboxylic acid, (1S,3R)-1-aminocyclopentane-1,3-dicarboxylic acid, (S)-4-carboxyphenylglycine, (2S,3S,4S)-CCG/(2S, 1'S,2'S)-2-(carboxycyclopropyl) glycine and (S)-4-carboxyphenylglycine. Preferably, the trans-1-aminocyclopentane-1,3-dicarboxylic acid is administered to the individual in an amount of from about 5 mg/kg to about 80 mg/kg. The method agonist (1S,3R)-1-aminocyclopentane-1,3-dicarboxylic acid is administered to said individual in an amount of from about 0.5 mg/kg to about 50 mg/kg. Concurrent with increase in uptake of glutamate by glial cells, the metabotropic glutamine receptor agonist decrease non-specific release of glutamate by glial cells. Generally, this method of the present invention is useful for an individual which has an neuronal injury which results in increased levels of extracellular glutamate. Representative examples of such neuronal injuries include head trauma, stroke, Parkinson's disease, Alzheimer's disease and epilepsy.

The present invention is also directed to a method of treating an individual having a pathophysiological state characterized by an increased level of extracellular glutamate, comprising the step of administering to the individual a therapeutically effective dose of a metabotropic glutamate receptor agonist.

Representative examples of such metabotropic glutamate receptor agonists include trans-1-aminocyclopentane-1,3-dicarboxylic acid, (1S ,3R)-1-aminocyclopentane-1,3-dicarboxylic acid, (S)-4-carboxyphenylglycine, (1R, 3S)-1-aminocyclopentane-1,3-dicarboxylic acid, (2S,3S,4S)-CCG/(2S, 1'S,2'S)-2-(carboxycyclopropyl) glycine and (S)-4-carboxyphenylglycine. Preferably, the trans-1-aminocyclopentane- 1,3-dicarboxylic acid is administered to the individual in an amount of from about 5 mg/kg to about 80 mg/kg. The method agonist (1S,3R)-1-aminocyclopentane-1,3-dicarboxylic acid is administered to said individual in an amount of from about 0.5 mg/kg to about 50 mg/kg. Concurrent with increase in uptake of glutamate by glial cells, the metabotropic glutamate receptor agonist decrease non-specific release of glutamate by glial cells. Generally, this method of the present invention is useful for an individual which has an neuronal injury which results in increased levels of extracellular glutamate. Representative examples of such neuronal injuries include head trauma, stroke, Parkinson's disease, Alzheimer's disease and epilepsy.

As used herein, the term "metabotropic glutamate receptor (mGluR)" shall refer to the class of G-protein linked-7-transmembrane glutamate receptors (Sheng, 1997).

It is specifically contemplated that pharmaceutical compositions may be prepared using a metabotropic glutamate receptor (mGluR) agonist according to the present invention. In such a case, the pharmaceutical composition comprises the mGluR agonist of the present invention and a pharmaceutically acceptable carrier. A person having ordinary skill in this art would readily be able to determine, without undue experimentation, the appropriate dosages and routes of administration of the mGluR agonist of the present invention. When used in vivo for therapy, the mGluR agonist of the present invention is administered to the patient or an animal in therapeutically effective amounts, i.e., amounts that eliminate or reduce the tumor burden. It will normally be administered parenterally, preferably intravenously, but other routes of administration will be used as appropriate.

The dose and dosage regimen will depend upon the nature of the injury and the levels of extracellular glutamate, as well as the characteristics of the particular agonist used to stimulate the mGlu receptors, e.g., its therapeutic index, the patient, the patient's history and other factors. The amount of agonist administered will typically be in the range of about 0.5 to about 80 mg/kg of patient weight. See Remington's Pharmaceutical Science, 17th Ed. (1990) Mark Publishing Co., Easton, Penn.; and *Goodman and Gilman's: The Pharmacological Basis of Therapeutics* 8th Ed (1990) Pergamon Press; which are incorporated herein by reference.

For parenteral administration, the mGluR agonist will most typically be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers and can be constructed according to methods well known to those having ordinary skill in the this art. The vehicle may contain minor amounts of additives such as substances that enhance isotonicity and chemical stability, e.g., buffers and preservatives. The mGluR agonist will typically be formulated in such vehicles at concentrations such that the final concentration is 0.5 mg/kg to about 80 mg/kg.

The following examples are given for the purpose of illustrating various embodiments of the invention and are not meant to limit the present invention in any fashion:

EXAMPLE 1

Materials Cell Culture and Glutamate Depleted Media

Cell culture supplies were obtained from Becton Dickinson (Franklin Lakes, N.J.) and Corning (Corning, N.Y.). NAD(P)H:FMN oxidoreductase, glutamate dehydrogenase and anti-neurofilament antibody were purchased from Boehringer Mannheim (Indianapolis, Ind.), S-4CPG, trans-ACPD, quisqualic acid, and cholera toxin (CTx) were obtained from RBI (Natick, Mass.). L-CCG-I, 1R3S-ACPD, 1S3S-ACPD, DHPG, L-AP4, L-CSA, (S)-α-methyl-4-carboxyphenylglycine (MCPG), α-methyl-L-CCG-I/(2S,3S, 4S)-2-methyl-2-(carboxycyclopropyl)glycine (MCCG) and (2S)-α-Ethylglutamic acid (EGLU) were purchased from Tocris Cookson (Bristol, UK). Other enzymes and chemicals were purchased from Sigma (St. Louis, Mo.) unless otherwise mentioned.

Primary cultures of rat postnatal hippocampal astrocytes were prepared from Sprague-Dawley rats. Both neonatal pups (P0–P3) and postnatal rats (P9–P40) were used. Animals were anesthetized with pentobarbital and decapitated, hippocampi were removed and freed of meninges, minced and digested in papain solution for 20–30 minutes as described (Ye et al., 1996). Cell initially plated in glutamine free culture media containing Earle's Minimum Essential Media (MEM) (Gibco/BRL, Gaithersberg, Md.), supplemented with 10% fetal bovine serum (FBS) (Hyclone, Logan, Utah.), 20 mM glucose, 10 U/ml penicillin and 10 μg/ml streptomycin. Media was changed two days after plating and every 3–4 days thereafter. To achieve essentially pure astrocyte cultures even from older postnatal animals, in which fibroblast contamination is a major problem (Lindsay et al. 1982), the growth of fibroblasts were inhibited by utilizing D-Valine substituted MEM supplemented with dialyzed FBS (Gilbert et al., 1975; Estin et al., 1986; Cholewinski et al, 1989). In this medium, fibroblast growth is retarded, since fibroblasts lack the enzyme to convert D-Valine (Gilbert et al., 1975). Briefly, 5 days after cell plating in regular culture media, the media of cells from >P15 rats was switched to 10% Dialyzed FBS+D-Valine MEM (Gibco). After about two weeks in D-Valine, the confluent culture was switched back to regular media. Cells were used after 2–3 weeks in culture, at which time >85–90% of cells were GFAP positive, and morphological identification and neurofilament staining did not show the presence of neurons in the cultures.

Glutamate analogues were applied in glutamate-depleted medium (GDM), in which [Glu] was <1 $\mu$M. Such glutamate-depleted medium was produced in confluent hippocampal astrocytes (P1–P3) cultured in 75 cm$^2$ flasks in which serum-containing media was incubated for 6–10 hours, collected and filtered through 0.2 $\mu$m bottom top filter. The media was either stored at 4° C. and used within one to two weeks or stored at –20° C. for later use.

EXAMPLE 2

Immunocytochemistry, Determination of Extracellular Glutamate Concentration, Glutamate/Aspartate Uptake and Release Cultures on glass coverslips were stained with antibodies against neurofilament or glial fibrillary acidic protein (GFAP; INCSTAR, Stillwater, Minn.) for cell identification. Expression of mGluRs was detected by anti-mGluR1$\alpha$ (against C-terminal peptide PNVTYASVILRDYKQSSSTL (SEQ ID No. 1)) and anti-mGluR 2/3 antibodies (against C-terminal peptide NGREVVDSTTSSL (SEQ ID No. 2)) (Chemicon; Temecula, Calif.). Briefly, cells were fixed for 10 minutes in 4% ice-cold paraformadehyde, washed in PBS and membrane permeablized in 0.1% TX-100 for another 10 minutes. Cells were then blocked for 1 hour in 10% normal goat serum in PBS and treated with primary antibodies overnight. The stainings were developed by ABC technique (Vectastain Elite ABC Kit from Vector Laboratories, Burlington, Calif.) and visualized with DAB (Vector Laboratories).

The bioluminescence method for detection was used for glutamate in solution as described by Fosse et al. (1986) with only minor modifications. The glutamate-specific reagent mixture contained potassium phosphate (pH 7.0) 25 mM, Triton X-100 40 $\mu$g/ml, dithiothreitol 100 $\mu$M, Myristyl aldehyde 40 $\mu$M (Aldrich; Milwaukee, Wis.), $\beta$-NAD 2 mM, ADP 250 $\mu$M, FMN 2.5 $\mu$M, luciferase 40 $\mu$g/ml, NAD(P)H:FMN oxidoreductase 400 mU/ml, glutamate dehydrogenase 0.5 mg/ml. All experiments were performed with a Monolight 2010 luminomitor (Analytical Luminescence Lab; Ann Arbor, Mich.).

For experiments in which [Glu]$_o$ concentrations were assessed by the bioluminescence method, cells were maintained in glutamate-depleted medium in the presence or absence of the agonists/antagonist combination of interest. To assess chronic effects, glutamate analogues were applied for 24 hours unless indicated otherwise. After the incubation period, the stimulation media (containing drugs of interest) were aspirated and cells were washed twice with MEM and allowed to remain for 30 to 60 minutes in drug free MEM supplemented with 20 mM glucose prior to taking media samples for glutamate measurements. To assess acute drug effects, untreated cells were washed and the reagent of interest applied in glucose supplemented MEM. Cells were harvested in 0.3 N NaOH and neutralized with 0.3 N HCl. Aliquots were stored in –20° C. for protein and [Glu]$_i$ determination. Glutamate standards used for calibration were prepared in MEM (For [Glu]$_i$ in 0.15 N NaCl). The drugs used in these studies did not interfere with the bioluminescence assay.

Uptake procedures were essentially identical to those previously described (Kimelberg et al. 1989; Ye et al., 1996). Briefly, 5–10 minutes before assessing uptake, astrocytes were washed and kept in a solution containing (in mM): NaCl 122, KCl 3, MgSO$_4$ 0.4, KH$_2$PO$_4$ 1.2, NaHCO$_3$ 25, D-glucose 10, and CaCl$_2$ 1.3, at 37° C., bubbled with 5%/95% CO$_2$/O$_2$. Then the cells were switched to the above solution supplemented with 0.1 mM D-aspartate and 0.4 $\mu$Ci/ml $^3$H-D-aspartate. Glutamate/aspartate uptake was determined over a 10 or 30 minutes period and was terminated by three quick washes, twice with ice cold 0.29 M sucrose solution with 10 mM Tris Nitrate, 0.5 mM Ca(NO$_3$)$_2$, (pH 7.40 by NaOH) and then with ice cold PBS. Cells were then harvested after a 30 minute incubation in 0.3 N NaOH solution (37° C.) and $^3$H activity was determined in a liquid scintillation counter (Beckman). Total uptake was normalized to protein content to eliminate variability due to cell number. Protein levels were determined using the bicinchoninic acid (BCA) assay (Pierce; Rockford, Ill.).

For experiments assessing high [K$^+$]$_o$ and low [Na$^+$]$_o$ effect on ACPD function (FIG. 3), equivalent KCl was substituted for NaCl. Some release experiments were carried out using $^3$H-D-Asp, similar to the approaches of Rutledge et al. (1996). Briefly, cells were preloaded in 100 $\mu$M D-Asp+0.8 $\mu$Ci/ml $^3$H-D-Asp solution for 30 or 60 minutes and then washed 3 times with the D-Asp- and $^3$H-D-Asp-free uptake media. Released D-Asp from cellular stores was assessed by measuring the radioactivity of $^3$H-D-Asp in solution and in cells.

EXAMPLE 3

Hippocampal Astrocytes Express mGluRs In Vitro

One objective of the present invention was to determine whether activation of mGluRs on astrocytes modulates glutamate transport. To establish the presence of mGluR receptors in the primary hippocampal astrocyte cultures used for these studies, monoclonal antibodies to mGluR receptors were used to identify their presence immunohistochemically. Consistent with previous reports in vivo (Petralia et al. 1996), selective labeling with both mGluR1$\alpha$ (group I) and mGluR2/3 (group II) specific antibodies (FIG. 1) was found. This suggests that both group I and II mGluRs are expressed in cultured hippocampal astrocytes.

EXAMPLE 4 mGluR Receptor Activation Reduces Extracellular Glutamate Concentrations

Figure 2A:
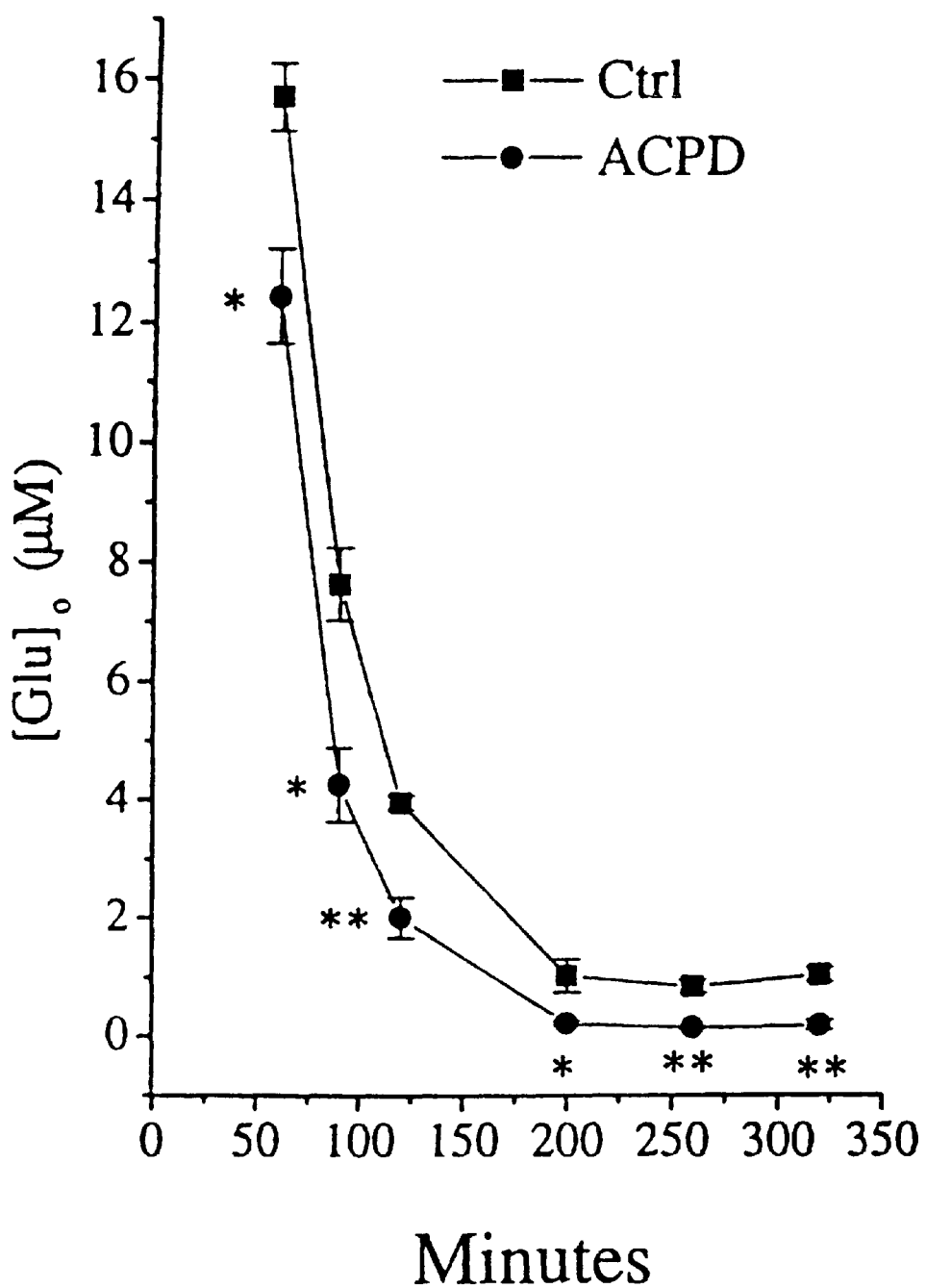
FIG. 2A shows hippocampal astrocytes were incubated with or without 500 μM t-ACPD for 24 hours. Culture media was removed and replaced with MEM+20 mM glucose+50 μM glutamate. Extracellular glutamate. ($[Glu]_o$) declined as a function of time due to astrocytic uptake (Mean±SEM, n=3 each).
Figure 2B:
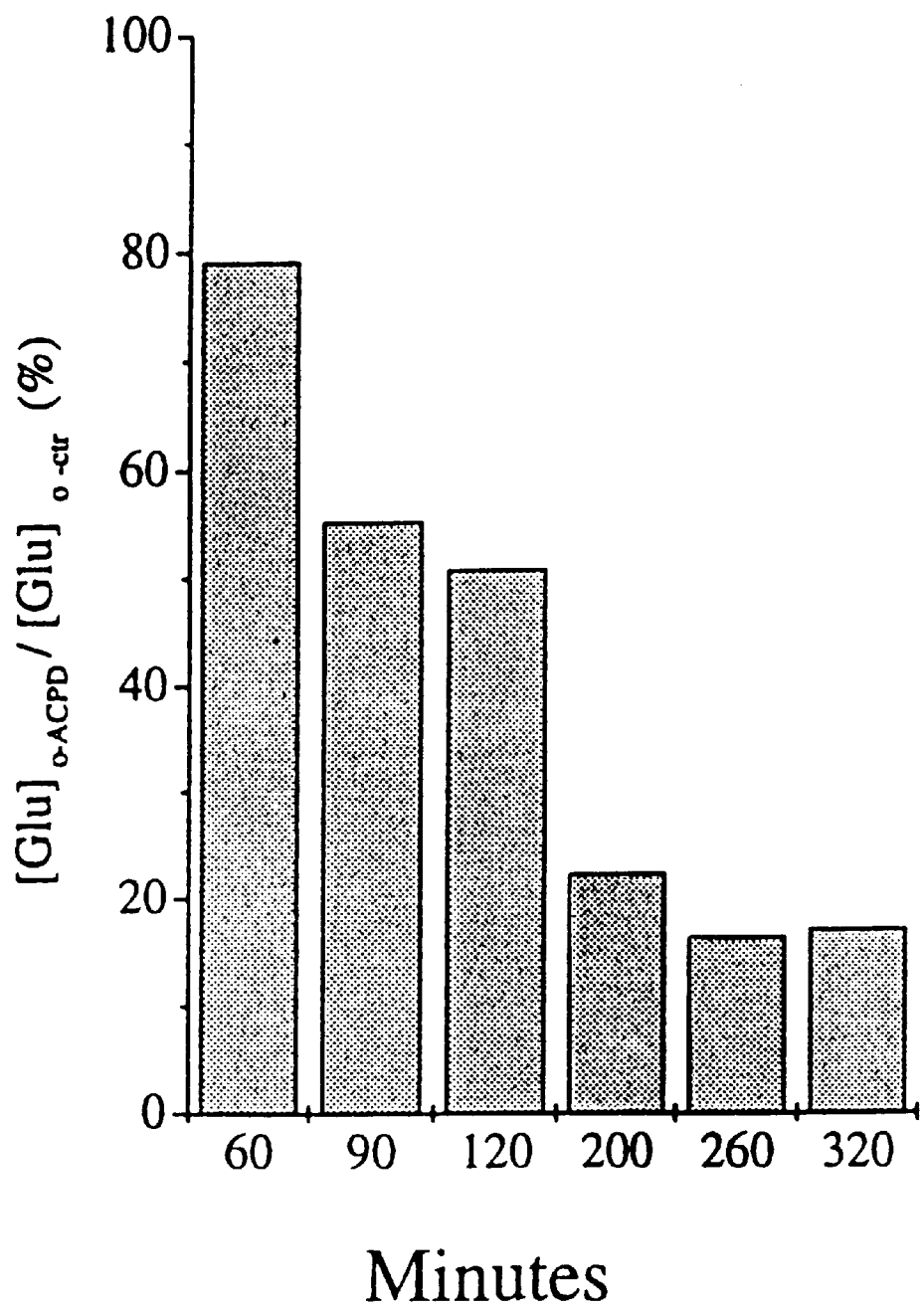
FIG. 2B shows the ratios of $[Glu]_o$ between ACPD treated and control cells in (FIG. 2A).

To delineate the role of mGluR receptors on [Glu]$_o$ levels, hippocampal astrocytes were challenged with 50 $\mu$M glutamate and cells that were pretreated with trans-ACPD were compared to control cultures (FIG. 2A). Control astrocytes rapidly remove glutamate from the medium, and after $\approx$3 hours, [Glu]$_o$ stabilized at values to 1 $\mu$M. Sister cultures treated for 24 hour prior to glutamate challenge with 500 $\mu$M trans-ACPD, the most commonly used mGluRs agonist, showed faster depletion of [Glu]$_o$, and the steady-state [Glu]$_o$ dropped to levels that were 5-fold lower than in control cultures (FIG. 2A). Mean values were 0.96±0.1 $\mu$M in control astrocytes, as compared to 0.18±0.03 $\mu$M in trans-ACPD treated astrocytes. The ratio of [Glu]$_o$ in ACPD treated cells versus control cells was plotted in FIG. 2B and shows the time-dependent decrease in [Glu]$_o$ with maximal effects after 200 minutes.

These data suggest that trans-ACPD increases the capacity of astrocytes to sequester glutamate and maintain a significantly lower steady-state [Glu]$_o$. Since [Glu]$_o$ is determined by the equilibrium of uptake and release, these effects could be explained by trans-ACPD stimulating uptake, reducing release, or both. A series of experiments was performed to address which of these possibilities account for the observed effects. First, the effects of trans-ACPD on glutamate release were examined. Astrocytes were exposed to glutamate/glutamine-free medium for 30–60 minutes and extracellular glutamate, which could have only been supplied by release from intracellular stores, was sampled over a 500 minute time period. 30–60 min after switching to MEM, the [Glu]$_o$ reached a new equilibrium.

Comparison of [Glu]$_o$ between ACPD treated and control groups from several representative experiments are given in Table 1. Treatment of astrocytes with ACPD consistently reduced the steady-state [Glu]$_o$ in release experiments. Interestingly, ACPD effects were more pronounced in astrocytes obtained from older animals, (e.g. >P13), than from neonatal animals. On average an ≈5-fold reduction in the steady-state [Glu]$_o$ was observed in astrocytes cultured from animals >P10, compared to 30–50% in astrocytes cultured from younger animals.

These results were confirmed by efflux studies in which $^3$H-D-Asp was used to ascertain the ratio of [Asp]$_o$/[Asp]$_i$. ACPD treated cells maintained a significantly higher [Asp]$_i$/[Asp]$_o$ ratio. The reduction of [Asp]$_o$/[Asp]$_i$ with trans-ACPD treated cultures was slightly less (20–50% of the control in 5 experiments) than the reduction in steady-state [Glu]$_o$.

Figure 2C:
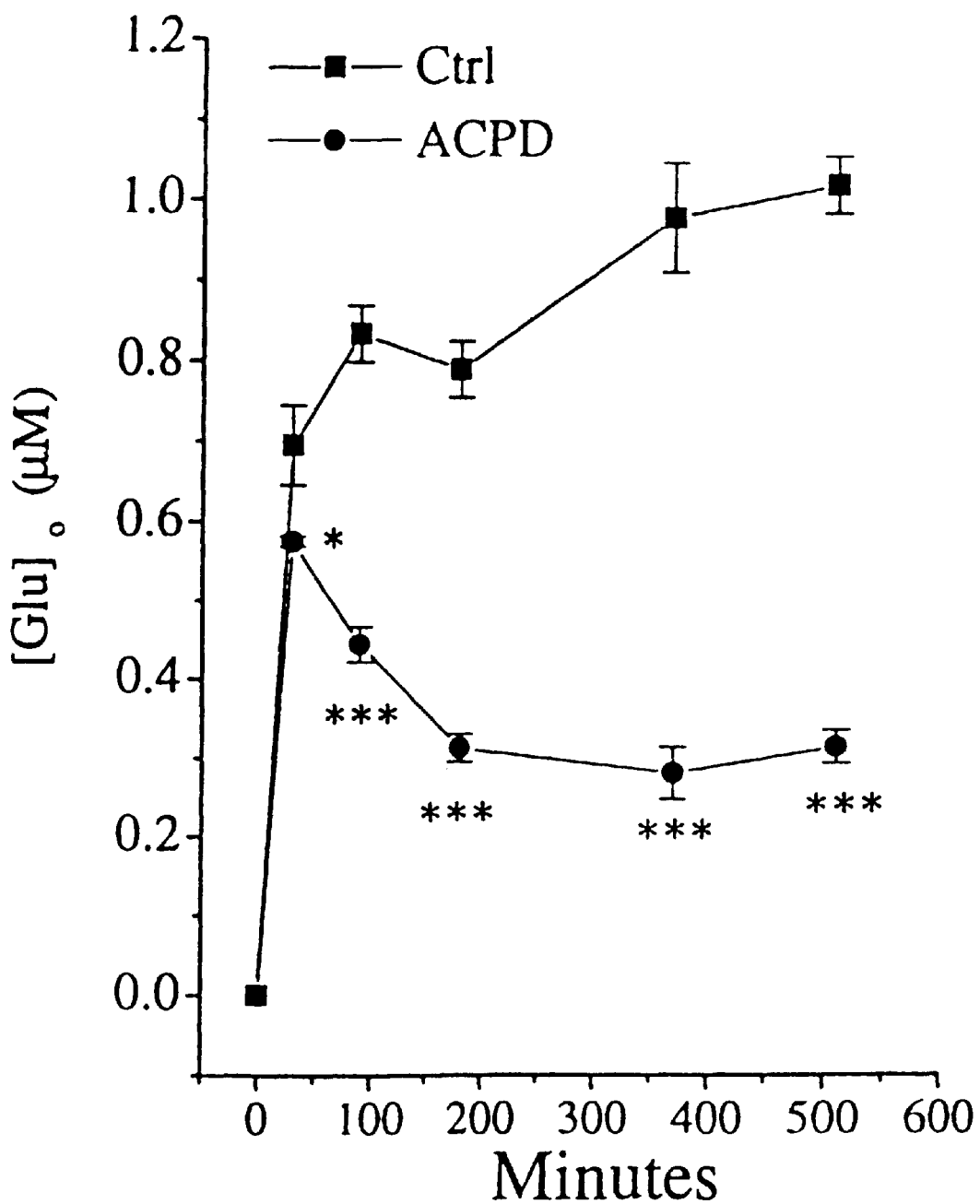
FIG. 2C shows the acute effects of ACPD on $[Glu]_o$. After the culture media had been replaced with glutamate free, glucose supplemented MEM, with or without 50 μM 1S3R-ACPD, $[Glu]_o$ increased as a function of time due to astrocytic release. Astrocytes receiving ACPD containing media established lower $[Glu]_o$ levels than untreated controls. (Mean±SE, n=6, * P<0.05;  P<0.01; * P<0.0001 by t-test, ACPD vs. control).

Moreover, these effects were observed in chronically (24 hours or longer) treated astrocytes. These studies were repeated to search for acute effects of ACPD. Glutamate levels were measured in astrocyte cultures that received glutamate-free, glucose-supplemented MEM, and sister cultures that in addition, received 50 μM 1S3R-ACPD in MEM. In control cells, [Glu]$_o$ increased gradually and reached steady-state levels of ≈0.8–1.0 μM after ≈90 minutes (FIG. 2C). Sister cultures treated with 50 μM 1S3R-ACPD also showed an initial increase in [Glu]$_o$. However, steady-state [Glu]$_o$ was achieved after ≈2 hours with significantly lower mean values of only 0.3–0.4 μM. These data suggest that acute and chronic ACPD application each markedly reduce the release of glutamate from astrocytes.

TABLE 1

Effects of ACPD in reducing extracellular glutamate level

| Age of Cells | Days in Vitro | [Agonist] μM | % of control [Glu]$_0$ |
|---|---|---|---|
| P0 | 60 | 100 t-ACPD | 60.6 ± 6.3 |
| P2 | 22 | 100 1S3R-ACPD | 73.4 ± 2.9 |
| P2 | 25 | 500 t-ACPD | 59.6 ± 10.1 |
| P2 | 28 | 500 t-ACPD | 78.2 ± 10.1 |
| P2 | 30 | 100 1S3R-ACPD | 66.9 ± 9.9 |
| P2 | 34 | 100 t-ACPD | 51.3 ± 5.7 |
| P9 | 18 | 250 t-ACPD | 46.3 ± 4.3 |
| P9 | 23 | 100 1S3R-ACPD | 45.8 ± 11.9 |
| P9 | 36 | 100 1S3R-ACPD | 66.5 ± 6.29 |
| P10 | 32 | 250 1S3R-ACPD | 24.1 ± 7.8 |
| P13 | 22 | 100 1S3R-ACPD | 34.1 ± 5.6 |
| P15 | 26 | 100 t-ACPD | 20.0 ± 6.1 |
| P15 | 24 | 250 L-CCG-I | 39.1 ± 4.4 |
| P16 | 20 | 10 1S3R-ACPD | 32.5 ± 4.7 |
| P21 | 19 | 100 t-ACPD | 23.1 ± 1.4 |
| P22 | 17 | 100 1S3R-ACPD | 17.3 ± 1.2 |

TABLE 1-continued

Effects of ACPD in reducing extracellular glutamate level

| Age of Cells | Days in Vitro | [Agonist] μM | % of control [Glu]$_0$ |
|---|---|---|---|
| P22 | 40 | 250 1S3R-ACPD | 29.0 ± 5.4 |
| P22 | 17 | 200 1S3R-ACPD | 14.8 ± 4.3 |
| P23 | 18 | 200 t-ACPD | 12.4 ± 1.2 |
| P40 | 31 | 100 t-ACPD | 19.5 ± 2.7 |

EXAMPLE 5

ACPD Modulates Na+-Dependent Glutamate Transporter In Astrocytes

Figure 3:
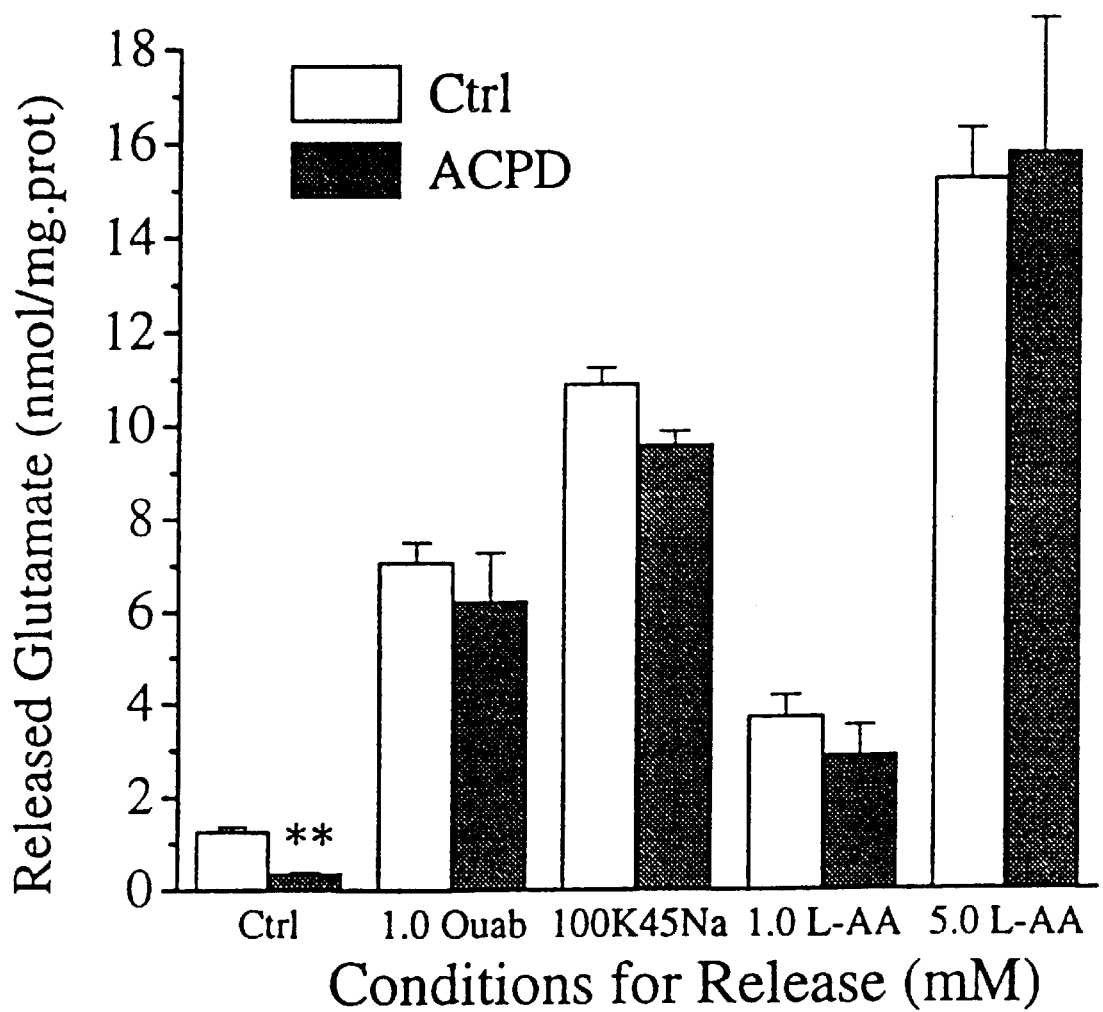
FIG. 3 shows that ACPD effects depend on normal transmembrane $Na^+$ gradient. Hippocampal astrocytes were treated with 200 μM 1S3R-ACPD for 24 hours and compared to untreated cultures. Glutamate release was determined in solution after a 30 minute treatment with the following: 1.0 mM Ouabain; 100 mM $K^+$/45 mM $Na^+$; 1.0/5.0 mM L-aminoadipic acid (L-AA) in MEM/glucose solution. (Mean±SE, n=6. ** P<0.001, ACPD vs. control). $[Glu]_o$ under all tested conditions was higher than in untreated cells and/or cells treated with ACPD alone, with P<0.01 (1.0 mM L-AA) and P<0.001 (all others).

To demonstrate that the modulatory effects of ACPD on extracellular glutamate levels were due to modulation of the astrocytic transporter, the effects of ACPD under unfavorable ionic conditions for Na$^+$-dependent transport were studied. The ionic gradient was disrupted by bathing cells in solution with (1) low extracellular sodium, [Na$^+$]$_o$ substituted with high [K$^+$]$_o$, (2) application of Ouabain or (3) poisoning of astrocytes with the glial specific toxin L-aminoadipic acid (L-AA). As expected for a Na$^+$-dependent electrogenic carrier, all of these conditions impaired glutamate uptake and resulted in elevated [Glu]$_o$ (FIG. 3). Most importantly, under these conditions, ACPD failed to modulate [Glu]$_o$, suggesting that ACPD effects depend on the normal operation of astrocytic Na$^+$-dependent glutamate transport.

Figure 4A:
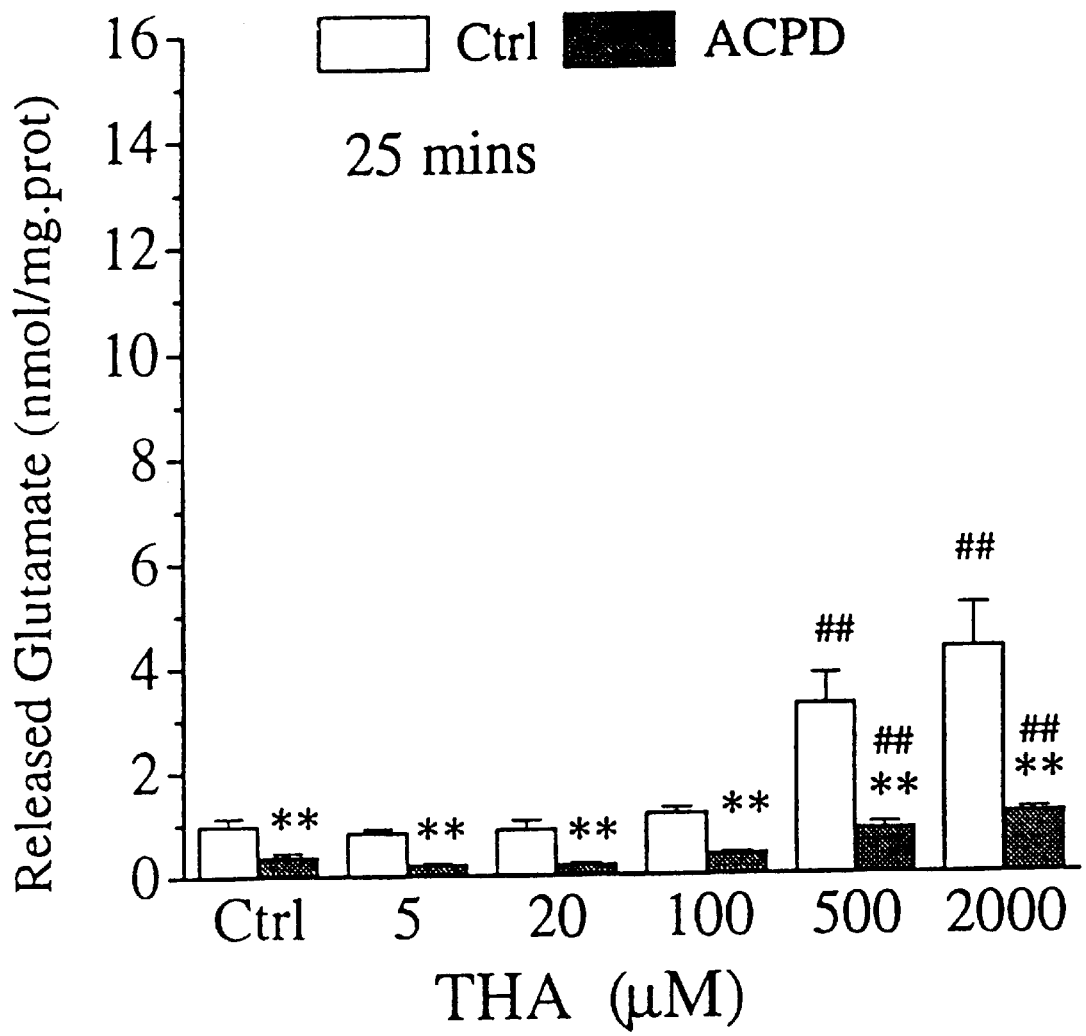
FIGS. 4A and 4B shows that the glutamate uptake-inhibitor DL-threo-β-hydroxyaspartate (THA) dose dependently increased glutamate release and THA treatment for 70 minutes (FIG. 4B), and induced more glutamate release than a 25 minute incubation (FIG. 4A). ACPD pretreatment persistently retarded THA induced glutamate release (n=4).

As these experimental conditions are somewhat non-physiological, the ACPD effect under physiological ionic conditions was assessed to establish whether ACPD effects were due to inhibition of release, stimulation of uptake, or both. Transportable glutamate uptake inhibitors were used, such as THA and PDC, which have been recognized as heteroexchange substrates for intracellular glutamate (Isaacson et al., 1993; Griffiths et al. 1994; Volterra et al. 1996; Velasco et al. 1996). Cells were incubated with THA (in glutamate free MEM) at concentrations ranging from 5–2000 μM, and glutamate release was compared between control cultures and cultures pretreated with 100 μM 1S3R-ACPD for 24 hours (FIGS. 4A and B). In line with previous reports, THA increased glutamate release from astrocytes in a dose- and time-dependent manner. Significant increases were observed with [THA] >100 μM, and at 70 minutes, THA induced more glutamate release than at 25 minutes. THA effects were observed in both control and ACPD treated cells. However, glutamate release was consistently about 3–5 fold lower in ACPD treated cells regardless of the THA concentration used. Similar effects were observed with PDC (data not shown).

The only source of glutamate to account for the dose-dependent accumulation of [Glu]$_o$ with increasing THA concentrations is intracellular glutamate released from the cells. Thus, ACPD predominantly affected the release of glutamate with little effect on uptake. This was confirmed by studying $^3$H-D-Asp uptake in the presence of THA. Indeed, the THA inhibition of uptake was identical in ACPD treated cells and controls (data not shown). In addition, THA- and PDC-induced release of glutamate did not significantly change the cellular glutamate content (102.9±12.1% and 110±14.7% of control after 70 minutes incubation with 500 μM PDC and THA, respectively).

Figure 4B:
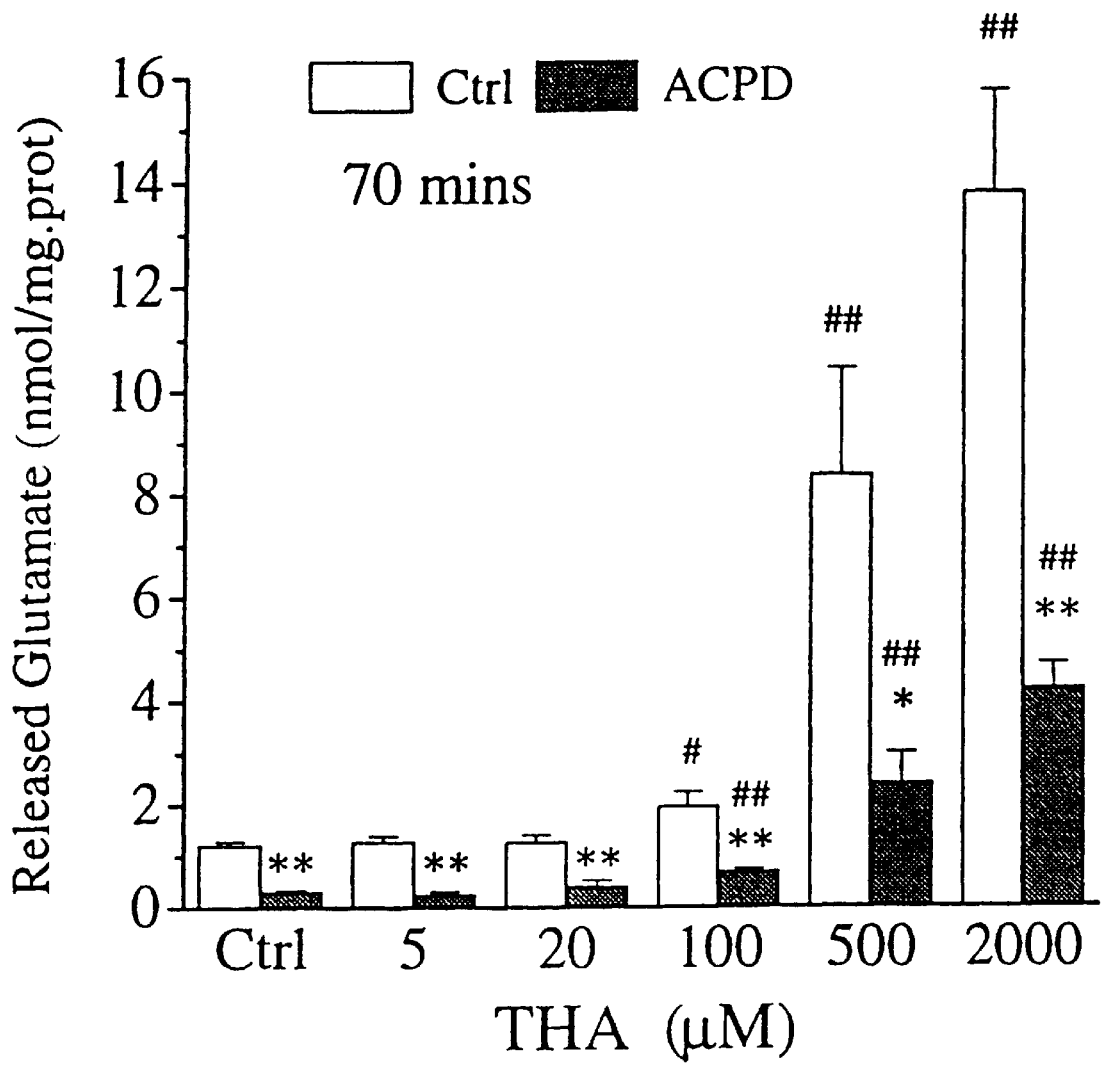
Figure 4C:
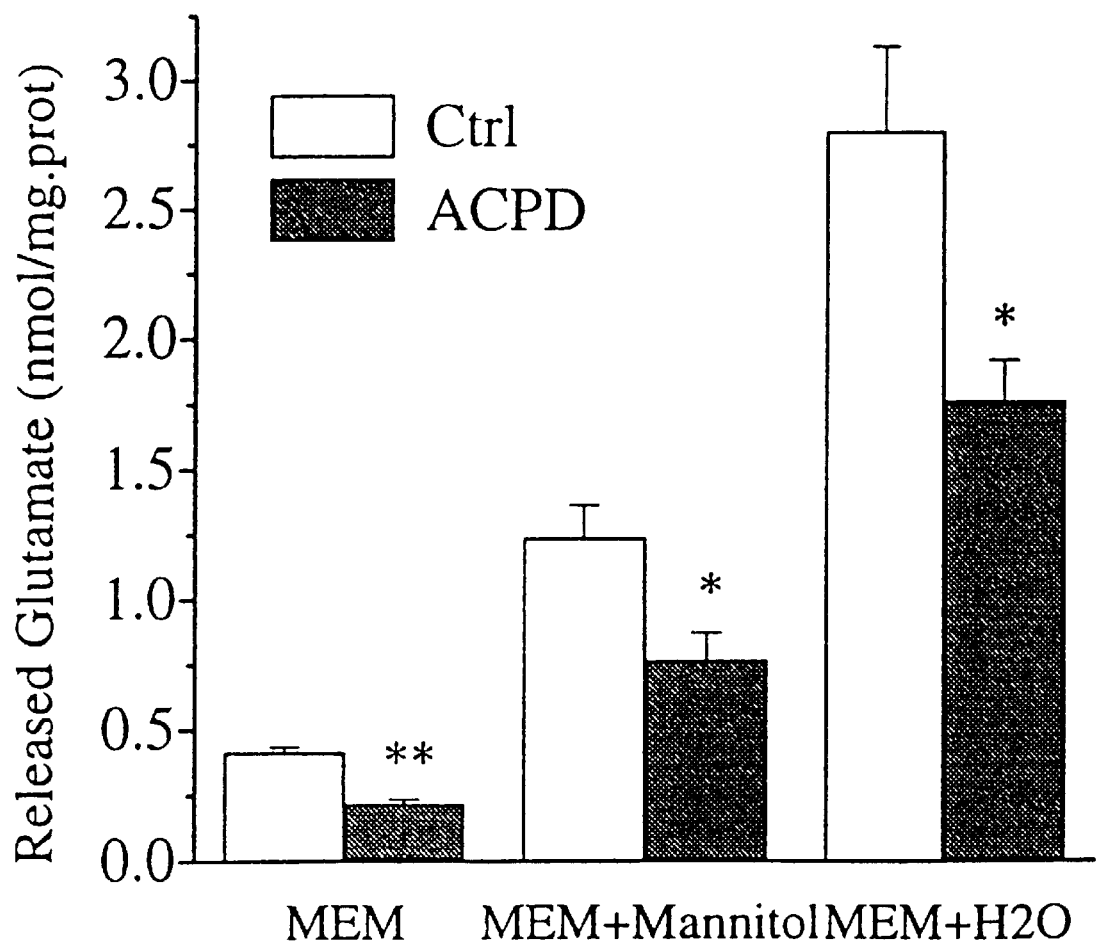
FIG. 4C shows that 15 minutes after 1S3R-ACPD (100 μM, 24 h) was washed off, cells were incubated in MEM vs. MEM+D-mannitol solution (v/v 1:2, restored NaHCO$_3$ and K$^+$ to normal, isotonic 290 mOsm) or MEM+H$_2$O (v/v 1:2, restored NaHCO$_3$ and K$^+$ to normal, 153 mOsm) to induce cell swelling. ACPD inhibited swelling induced glutamate release to some extent (n=6).

In addition to reversal of the Na$^+$-dependent carrier, a second pathway has been identified for glutamate release from astrocytes, which is dependent on cellular swelling-induced anion transport (Kimelberg et al. 1990; Rutledge et al., 1996). To show whether ACPD influences swelling-induced glutamate release, cells were exposed to hypotonic solution and [Glu]$_o$ was compared in control and ACPD treated cultures. [Glu]$_o$ increased 6-fold after a 15 minute hypotonic (153 mOsm) challenge (FIG. 4C). Interestingly, ACPD pretreatment decreases the swelling-induced glutamate release to some extent. However, this effect was much smaller and can be explained by the depolarization of the cells due to swelling, which will result in the reversal of the Na$^+$-dependent glutamate transport (Kimelberg et al., 1988). ACPD effects on swelling-induced release of glutamate may contribute to the modulation of glutamate transporter by ACPD. As shown in FIG. 3, 45 mM [Na$^+$]$_o$/ 100 mM [K$^+$]$_o$ abolished ACPD effects. Low [Na$^+$]$_o$ (>20 mM) alone was insufficient to completely abolish ACPD effect.

Figure 4D:
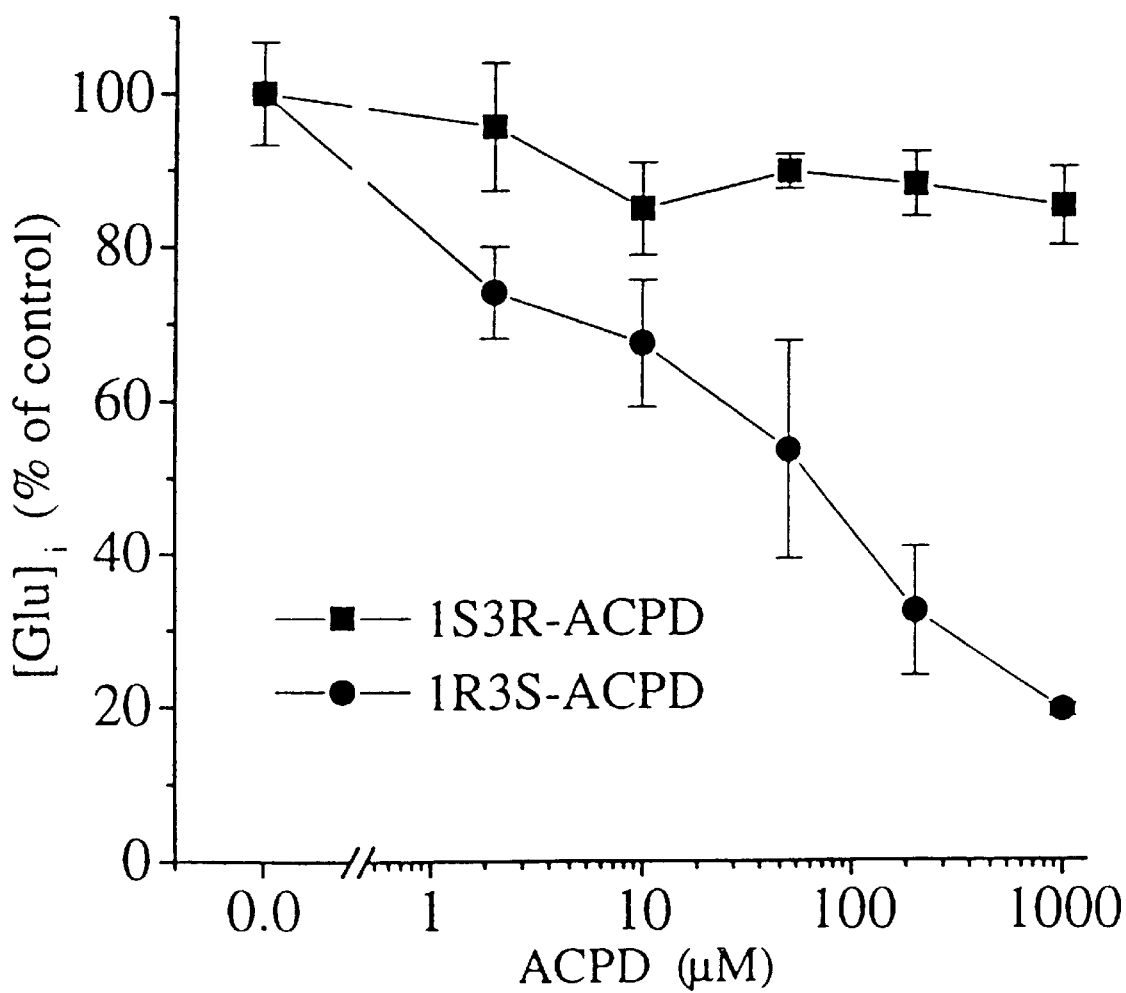
FIG. 4D shows that 1S3R-ACPD pretreatment did not affect intracellular glutamate content. However, the inactive isomer 1R3S-ACPD dose-dependently decreased [Glu]$_i$ (n=6, mean±SE, * P<0.05, ** P<0.01, ACPD vs. control; # P<0.05, ## P<0.01 by t-test, THA vs. control.)

Since the decreased [Glu]$_o$ in ACPD treated cells could simply have resulted from decreased intracellular glutamate content, the impact of chronic treatment with ACPD on intracellular glutamate levels was studied. Surprisingly, 1R3S-ACPD, but not 1S3R-ACPD, significantly reduced intracellular glutamate content. As shown in FIG. 4D, even at the highest dose used (1 mM), 1S3R-ACPD only slightly reduced the intracellular glutamate content (85.2±5.1% of control), whereas the inactive stereosiomer 1R3S reduced it to 18.4±0.9%. These data suggest that the reductions of glutamate efflux by 1S3R-ACPD pretreatment are not due to reducing intracellular glutamate stores. However, the modest reduction of [Glu]$_o$ by high doses of 1R3S-ACPD (FIG. 7A) may be explained by the reduction of [Glu]$_i$.

EXAMPLE 6
ACPD Rectifies Astrocytic Glutamate Transport

Figures 5A, 5B:
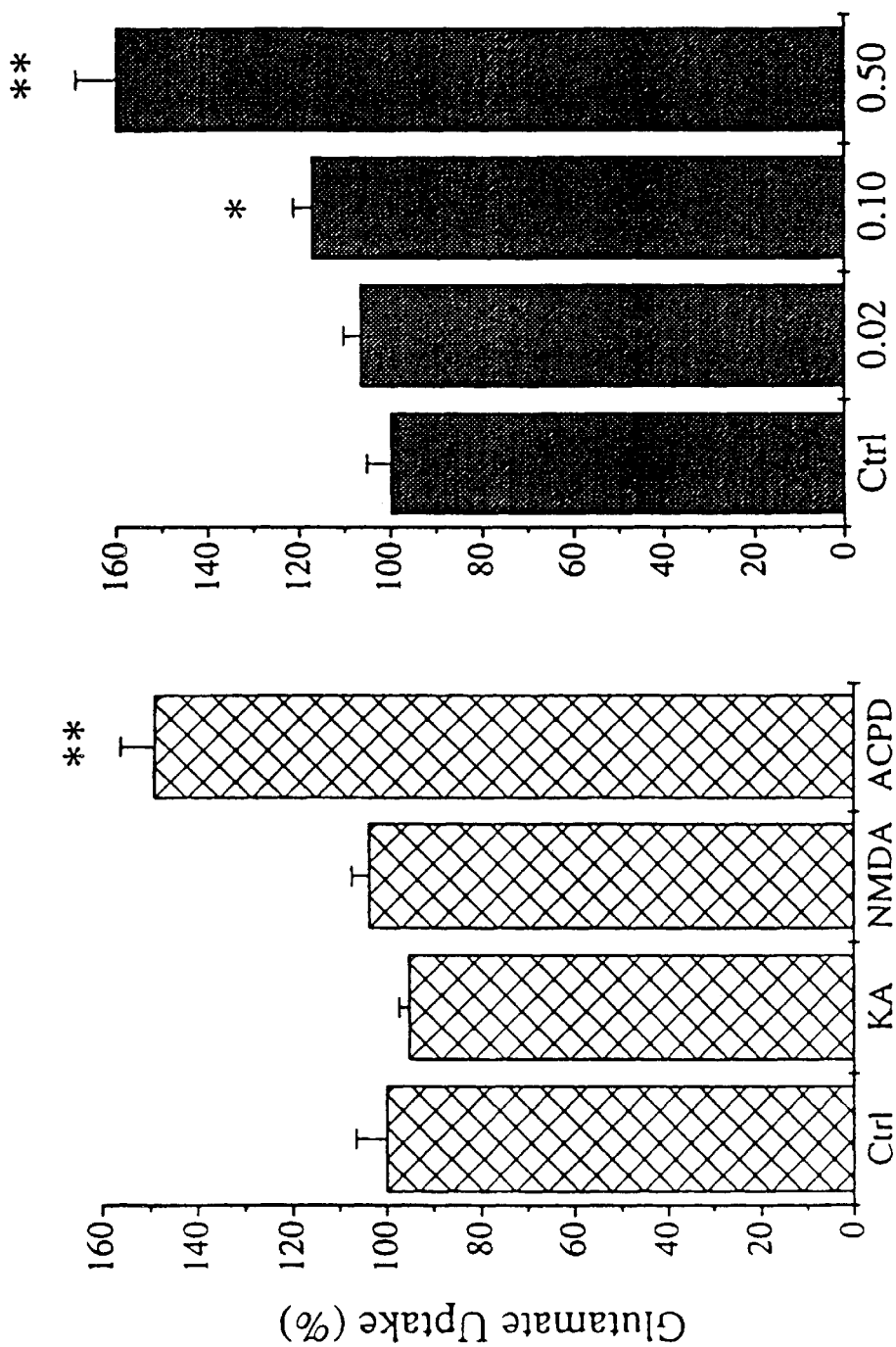
(FIG. 5A). Cells treated for 24 hours with 0.5 mM KA, NMDA or t-ACPD.
(FIG. 5B). 48 hours incubation with 0.02–0.5 mM t-ACPD.
Figure 5C:
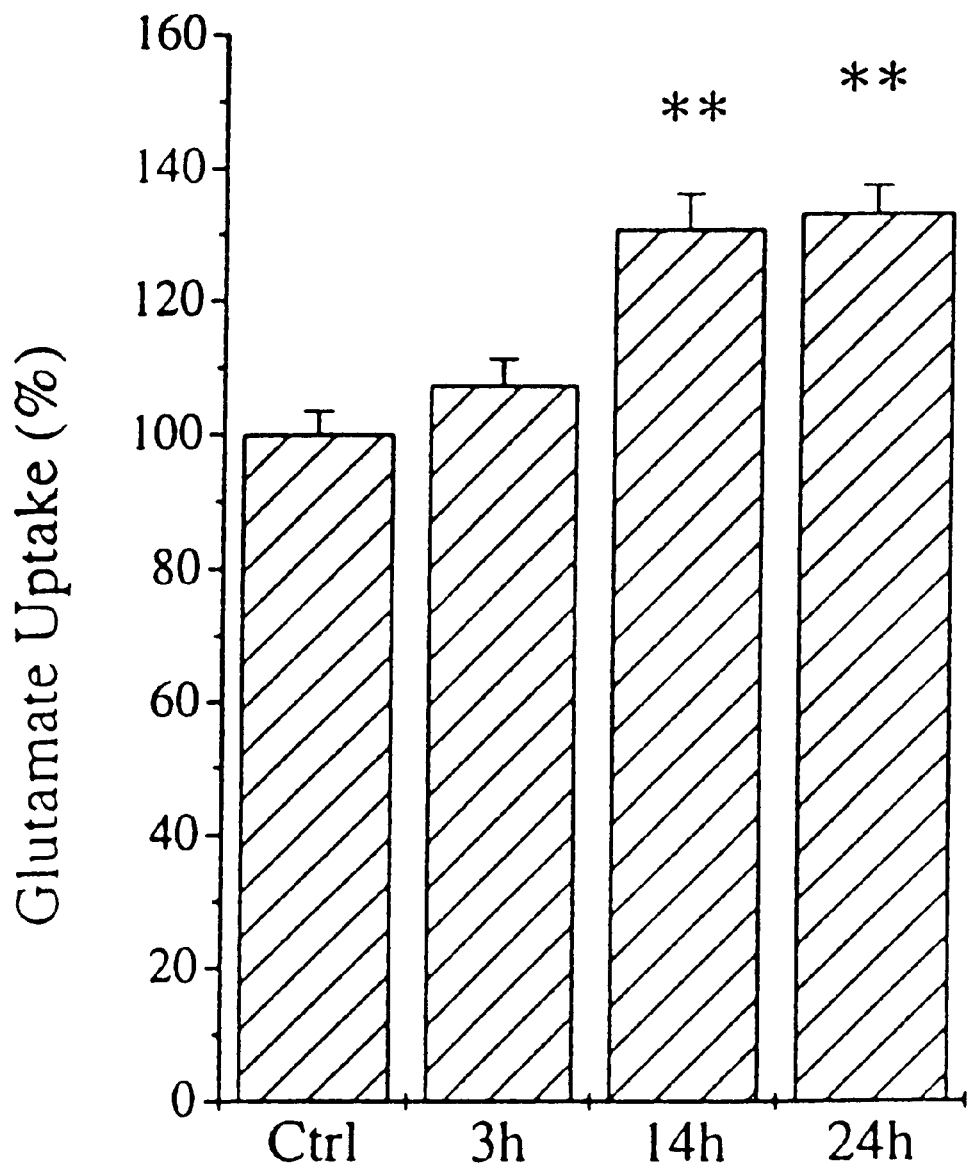
(FIG. 5C). Incubation with 0.5 mM trans-ACPD for 3–24 hours. (Mean±SE, n=6,  P<0.05,  P<0.001, t-test).

The above experiments clearly demonstrate that ACPD reduces glutamate release. To unequivocally assess ACPD effects on glutamate uptake, the unidirectional transport of $^3$H-aspartate in ACPD treated astrocytes was compared to control cells. After a 24 hour exposure of cells to 0.5 mM trans-ACPD or 1S3R-ACPD, glutamate/aspartate uptake was enhanced by 31.0±2.7% of control (average of 25, mean values range from 14.6% to 65.6%) in 25 out of 29 experiments (each with n=4–6). The other 4 experiments showed small but statistically insignificant increases (5–10%). Cultures included a range of preparations derived from P1–P36 rats and time in culture ranged between 15–34 days. ACPD effects were significantly larger in astrocytes isolated from animals >P9 than those from neonatal rat pups (35.2%±3.8%, n=11, vs. 24.5%±2.4%, n=14; p<0.05). No significant effects on aspartate uptake using KA or NMDA (1 mM, 5/5 experiments, FIG. 5A), or 1R3S-ACPD were observed.

mGluR activation by trans-ACPD or 1S3R-ACPD increased glutamate uptake in a close and time dependent manner (FIGS. 5B and 5C). ACPD enhancement of uptake was significantly slower and required larger doses ($\approx$500 $\mu$M) than those used to reduce glutamate release. In addition, unlike the reduction of glutamate release, acute ACPD application of up to 3 hours was ineffective in enhancing uptake. Taken together, the above data suggest that ACPD "rectifies" the movement of glutamate and alters the transporter to prefer influx over release, consequently resulting in significantly lower steady-state levels of [Glu]$_o$.

EXAMPLE 7
ACPD Effects Are Long Lasting

Figure 6:
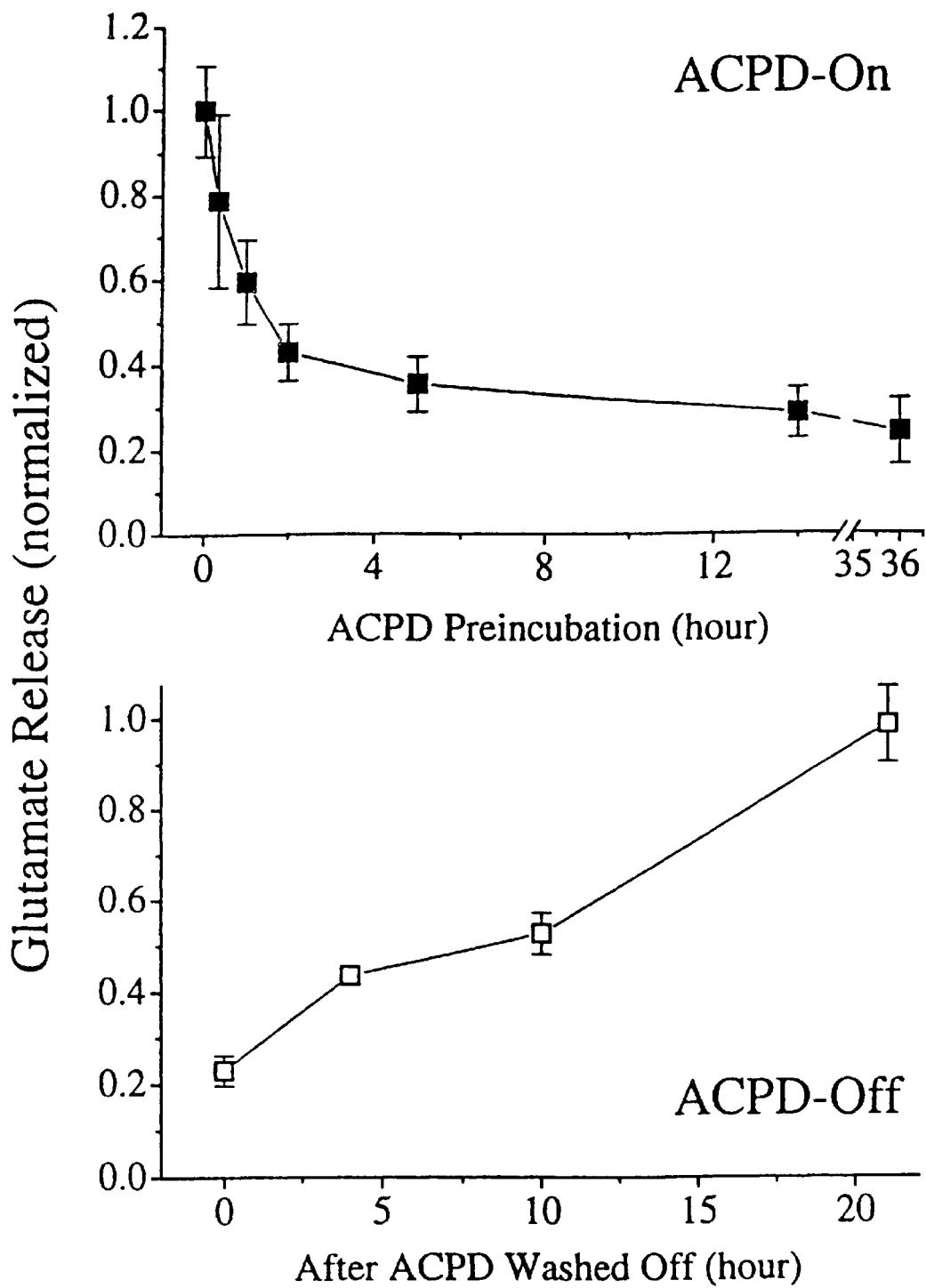
FIG. 6 shows that ACPD effects develop gradually and persist for several hours after removal of ACPD. Normalized glutamate release plotted as a function of preincubation time (ACPD-On curve) showed maximal ACPD effect after >6 hours. ACPD effects persisted for over 10 hours (ACPD-Off curve).

Since acute and chronic exposure to ACPD was effective in reducing [Glu]$_o$, the time dependence of ACPD effects was evaluated in more detail. ACPD attenuation of glutamate release as a function of preincubation time was examined. 200 $\mu$M 1S3R-ACPD was applied to cultures for 0.5–36 hours prior to determining extracellular steady-state glutamate levels. A representative example is shown in FIG. 6 (on-curve) illustrating that attenuation of [Glu]$_o$ increases with increasing preincubation times, with an ET$_{50}$ of $\approx$1 hour and maximal effects after $\approx$14 hours when ACPD reduced [Glu]$_o$ levels to <30% of control. Longer ACPD incubation (36 hours) did not further attenuate [Glu]$_o$.

The experimental paradigm used throughout these studies showed attenuation of [Glu]$_o$ by preincubation with ACPD, but the changes were determined in the absence of ACPD, suggesting that ACPD effects are persistent. To determine how long ACPD effects persist, the off-rate of these effects was determined experimentally. Cultures received ACPD for 24 hours, they were washed 3 times with glutamate-depleted medium for 0.5–24 hours (FIG. 6B, "off" time shown in x-axis), and then switched to MEM/glucose for 60 minutes to assess the release of glutamate. As shown in FIG. 6B, the effect of ACPD gradually returned to control levels after about 20 hours in ACPD free glutamate-depleted medium. 50% of the effect remained 10 hours after ACPD had been washed off. These data suggest that ACPD effects persist over several hours.

As shown in FIG. 2A, the persistence of ACPD effects allowed treated astrocytes to reduce [Glu]$_o$ below control levels, even in the face of an exogenous glutamate challenge. This suggests that astrocytes treated with ACPD have a considerable capability for sustained removal of extracellular glutamate and can maintain it at a lower levels than untreated controls.

EXAMPLE 8
ACPD Effect Can Be Mimicked By Other Group II mGluR Agonists

Figure 7A:
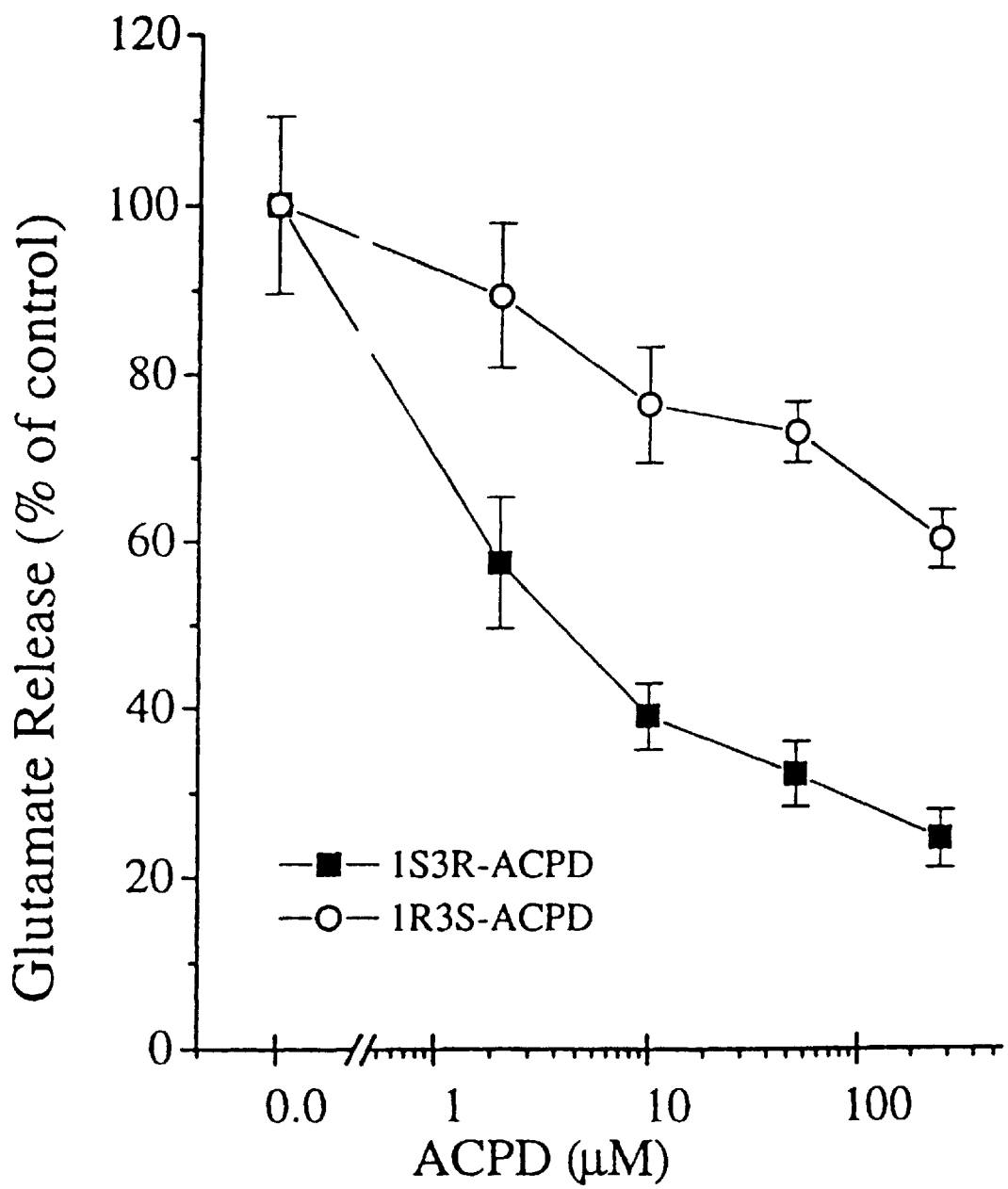
(FIG. 7A). 1S3R-ACPD was ≈100-fold more effective than 1R3S-ACPD in reducing glutamate release from astrocytes (n=6, mean±SE).

Trans-ACPD is a compound that contains an equivalent mixture of 1S3R- and 1R3S-ACPD. Typically, the 1S3R form is much more potent than the 1R3S form. Dose-effect curves were established for both isomers on sister cultures by monitoring glutamate release according to the procedures described above. As shown in FIG. 7A, 1S3R-ACPD was highly effective and reduced glutamate release in a dose dependent-manner, with an EC$_{50}$$\approx$2–5 $\mu$M. By contrast, 1S3R-ACPS was about 2 orders of magnitude less effective, with concentrations >50 $\mu$M of 1R3S-ACPD required to achieve any significant effect.

Figure 7B:
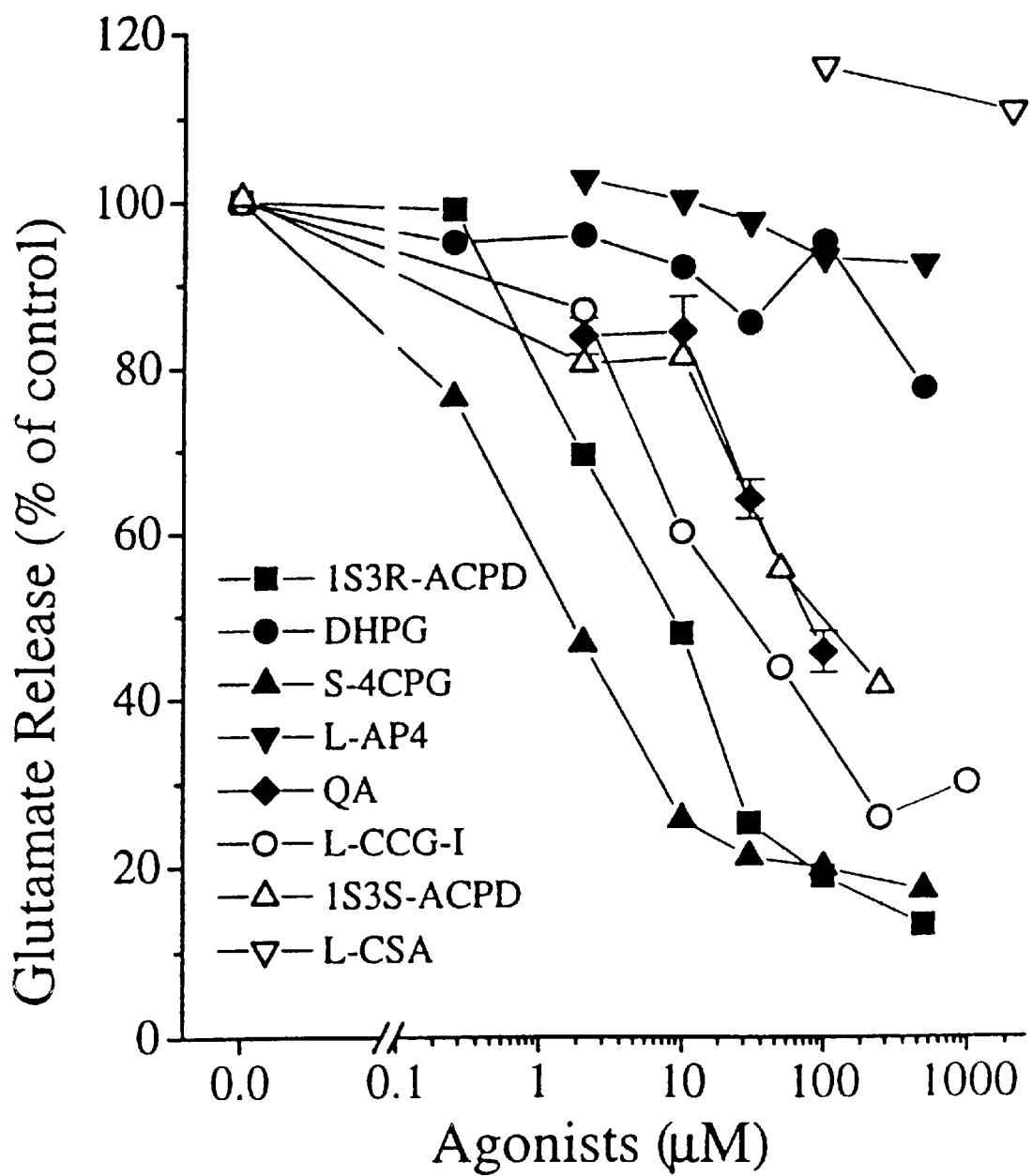
(FIG. 7B). Several tested compounds mimicked ACPD effect. In the order of potency they were: S-4CPG>1S3R-ACPD>L-CCG-I>1S3S-ACPD=QA. DHPG, L-AP4, and L-CSA were without effect (mean, n=4–6).

ACPD is the most commonly used group I and group II metabotropic glutamate agonist. In order to characterize which mGluRs subtypes may account for the observed effects, other mGluRs agonists were evaluated. The agonists used for these studies included: DHPG, reported to be a group I mGluRs specific agonist (Jung et al. 1996); Quisqualic acid (QA), 1S,3S-ACPD, S-4CPG (group II agonist and group I antagonist (Merlin et al. 1995)), L-CCG-I (group II agonist), L-AP4 (specific group III agonist (Bushell et al. 1996)) and L-CSA (which activates phospholipase D-coupled receptors and may increase cAMP level in hippocampus (Boss et al. 1994; Boss et al., 1995)). Cells were treated for 24 hours with these compounds and then switched to MEM as described above for ACPD. The dose-effect curves for these compounds were summarized in FIG. 7B. Five compounds presumed to be group II mGluRs agonists all reduce [Glu]$_o$ in a dose-dependent manner. The order of apparent efficacy in reducing glutamate release was S-4CPG<1S3R-ACPD<L-CCG-I<QA=1S3S-ACPD. The potency of 1S3S-ACPD was between that of 1S3R-ACPD and 1R3S-ACPD. DHPG, L-AP4 and L-CSA were ineffective (FIG. 7B) as were the ionotropic agonists NMDA and KA (Data not shown).

Figure 8B:
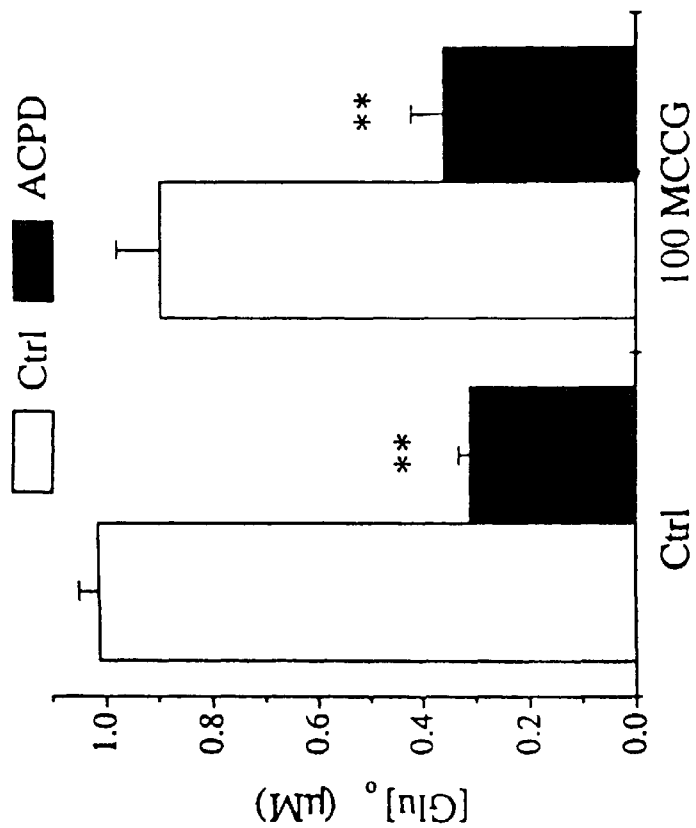
FIG. 8 shows that the commonly used mGluR antagonists MCPG (FIG. 8A), and the more specific mGluR II antagonist, MCCG (FIG. 8B), did not block ACPD effects (n=6).
(FIG. 8C) Incubation with pertussis toxin 6 h prior to and during treatment with ACPD did not block ACPD effects (n=4). (Mean±SE, * P<0.05, **P<0.001, ACPD+PTx vs. control; p=0.0766 among ACPD+PTx (0–500 ng/ml), ANOVA).
Figure 8A:
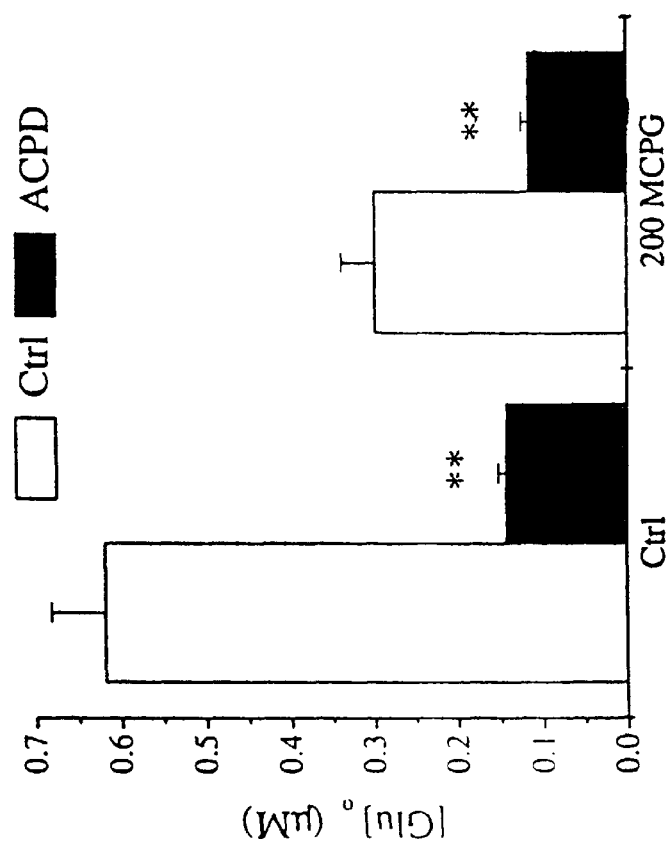

EXAMPLE 9
ACPD Effects On [Glu]$_o$ Are Insensitive To PTx And Do Not Require Protein Synthesis The effects of ACPD are likely to be mediated by activation of group II mGluRs. To further examine group II mGluR involvement and the underlying signaling pathway, several known mGluR antagonists and drugs that inhibit defined signal transduction events underlying mGluR effects were used. While the agonist studies strongly suggest a group II involvement, the presumed group II specific mGluR antagonists, EGLU (Manahan-Vaughan, 1997), MCCG (Jane et al. 1994), and MCPG, were unable to suppress ACPD effects on [Glu]$_o$ when applied simultaneously with ACPD (FIGS. 8A and 8B). MCPG, MCCP and EGLU also failed to inhibit the effect of other mGluR agonists, such as L-CCG-I (data not shown).

Figure 8C:
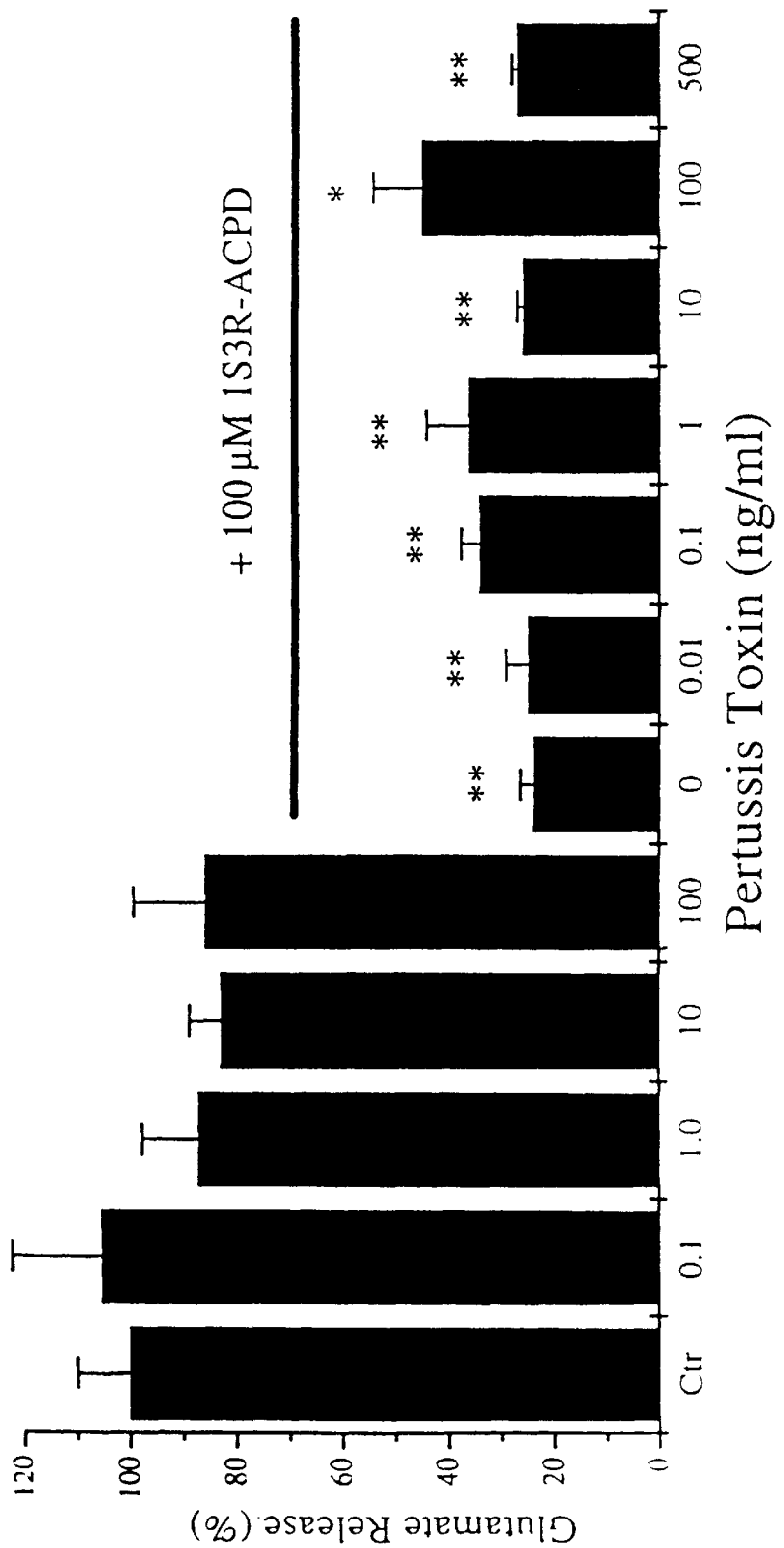

Several studies showed that mGluR mediated responses are sensitive to pertussis toxin (PTx; Schoepp et al., 1993), which disrupts G protein activity. In these experiments (FIG. 8C) pertussis toxin (0.01–500 ng/ml added 6 hours prior to ACPD) failed to inhibit ACPD modulation. Even if pertussis toxin was applied after ACPD had been washed off, it still failed to reverse the modulatory effects of ACPD. Thus the effect are unlikely mediated by a pertussis toxin sensitive G-protein.

Figure 9A:
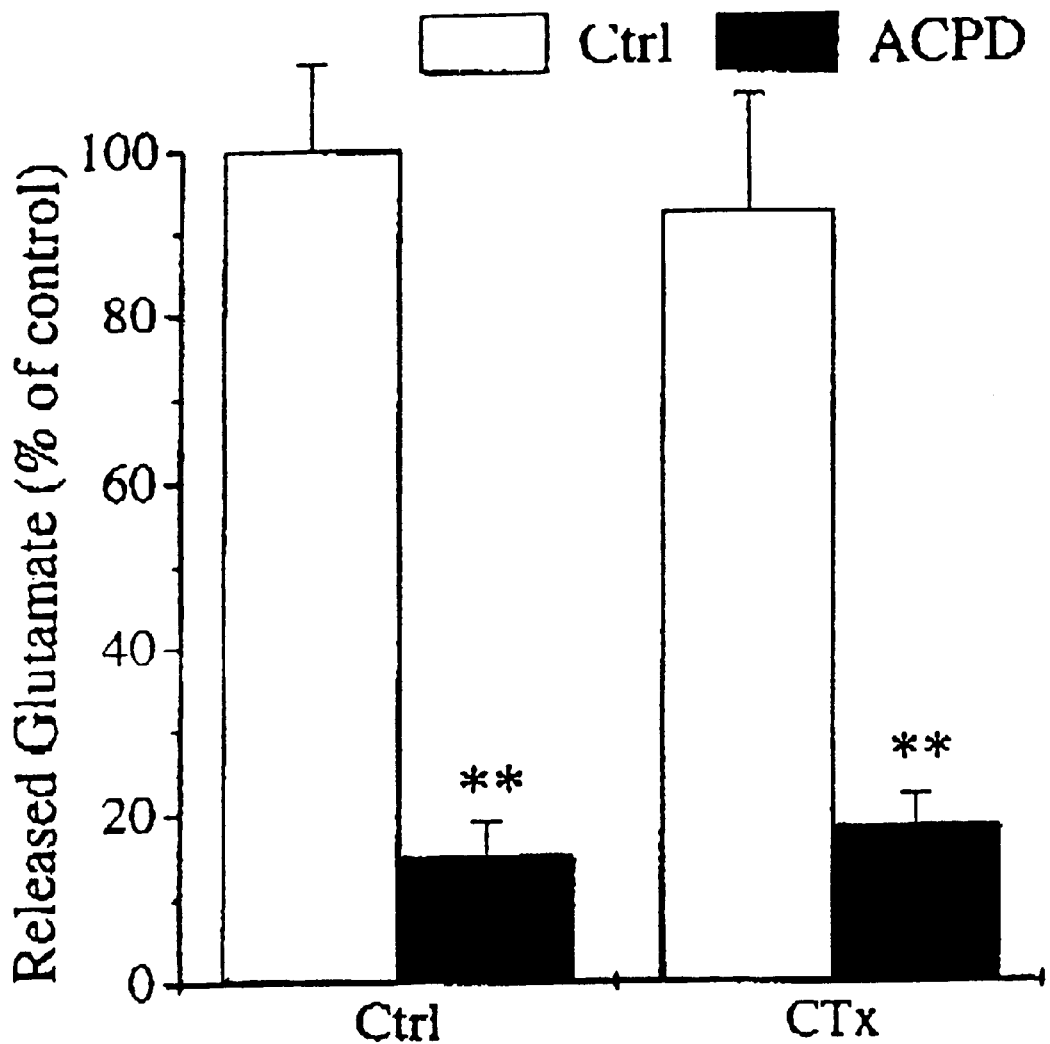
(FIG. 9A). Cholera toxin (CTx; 2 ng/ml) did not inhibit ACPD (100 μM 1S3R-ACPD) effects.
Figure 9B:
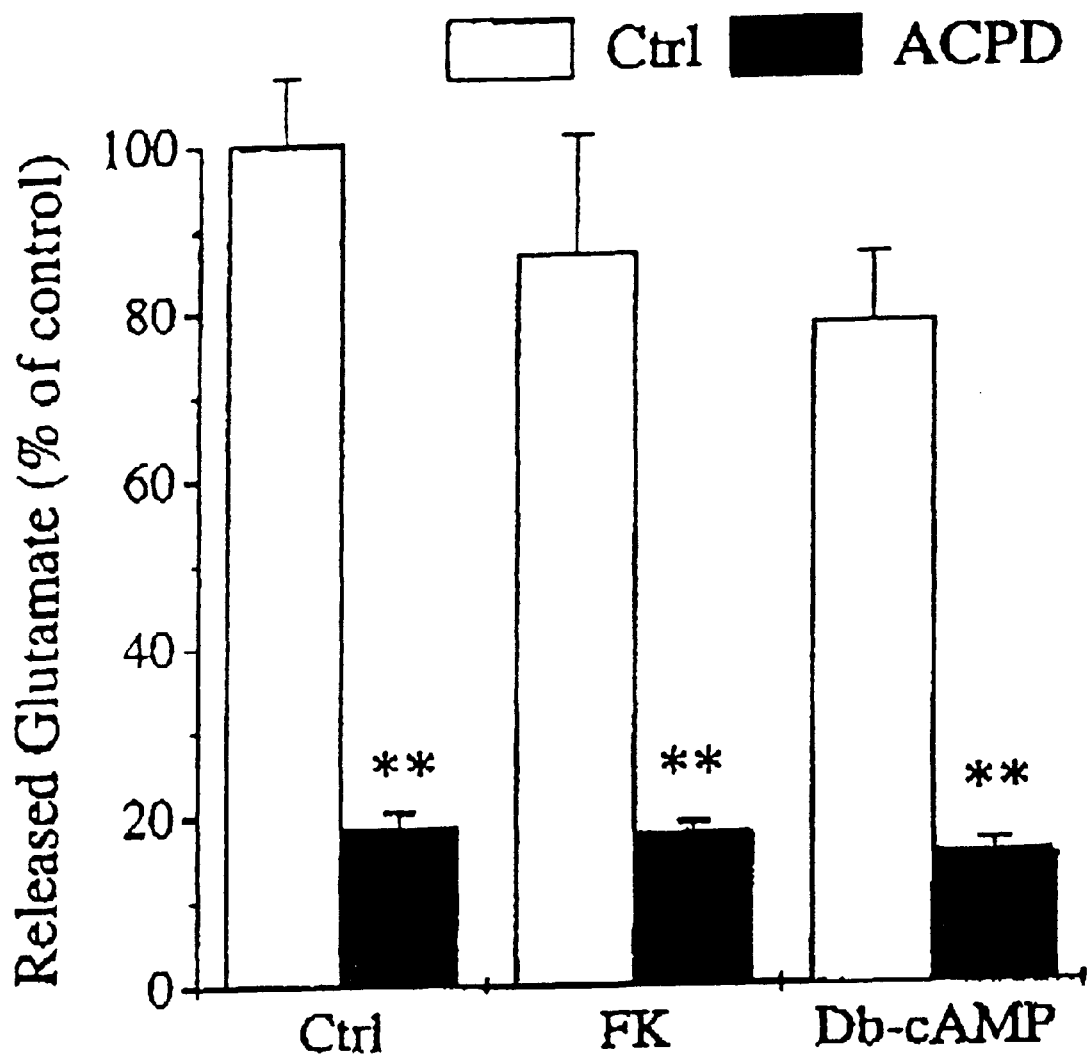
(FIG. 9B). Co-incubation with Forskolin (10 μM) or Db-cAMP (0.2 mM) did not block ACPD effects.
Figure 9C:
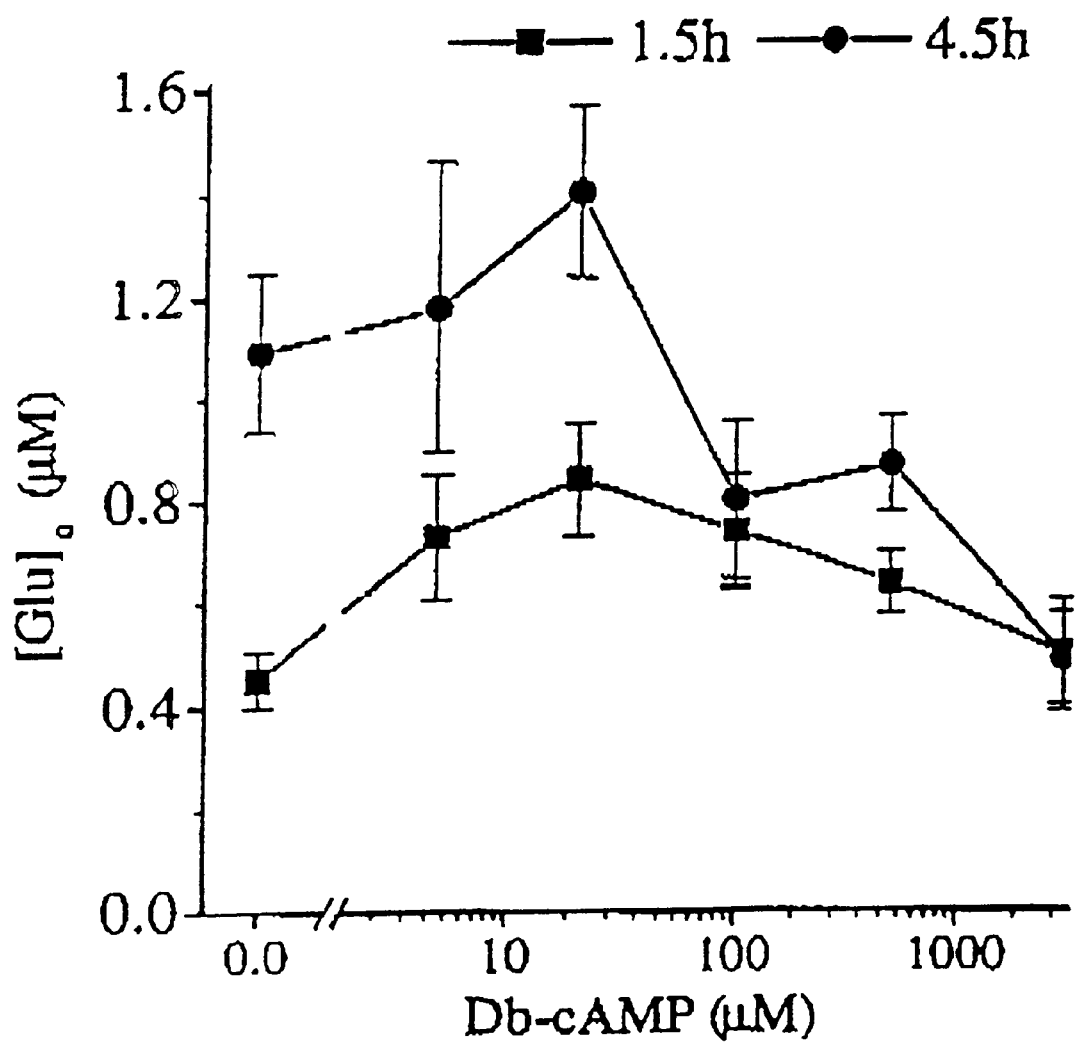
(FIG. 9C). Db-cAMP did not significantly affect [Glu]$_o$ level over a large concentration range.
Figure 9D:
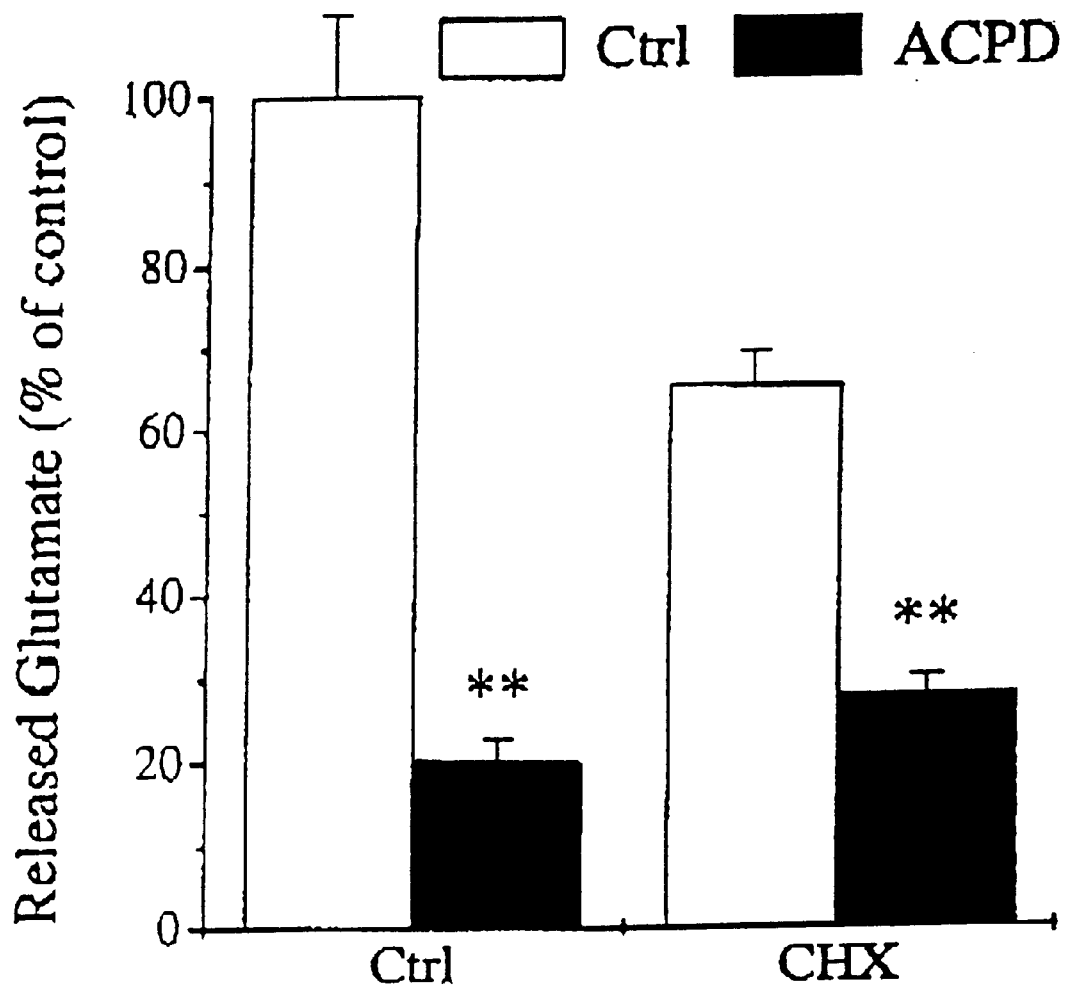
(FIG. 9D). Inhibition of protein synthesis with cycloheximide (CHX; 2 μg/ml) did not block ACPD effects. (Mean±SE, n=6, ** P<0.001, ACPD vs. control, t-test).

To examine a possible involvement of cAMP, the ACPD effects were mimicked with drugs that modulate cAMP levels, such as cholera toxin (CTx; Gebicke-Haerter et al. 1994; Deryugina et al., 1996), Forskolin, and Dibutylyl-cAMP (Db-cAMP). As shown in FIG. 9A, 2.0 μg/ml cholera toxin neither inhibited nor mimicked ACPD effects. Similarly, Forskolin and Db-cAMP neither blocked nor facilitated the ACPD effects on [Glu]$_o$. (FIG. 9B). Changing cAMP levels using the membrane permeable Db-cAMP alone did not significantly change [Glu]$_o$, even at the highest concentration tested (3 mM; FIG. 9C). These data suggest that the ACPD effects on glutamate transport are not due to modulation of cAMP levels. This is also supported by the fact that ACPD effects were insensitive to pertussis toxin. Previous studies suggest that mGluRs-induced cAMP changes are sensitive to pertussis toxin (Baba et al. 1993; Huttenlocher et al. 1996). Finally, ACPD effects on [Glu]$_o$ do not require protein synthesis, as incubation with the protein synthesis inhibitor cycloheximade (CHX; 2 μg/ml) could not inhibit the ACPD induced attenuation of [Giu]$_o$ (FIG. 9D).

EXAMPLE 10
ACPD Effect Can Be Mimicked By Glutamate, The Endogenous Ligand For mGluRs Glutamate undoubtedly is the endogenous ligand for mGluRs. However, it was necessary to establish whether glutamate itself can induce the modulation in glutamate levels observed, and thus can mimic the modulatory effects observed with ACPD. These studies are difficult since, unlike ACPD, glutamate is also a substrate for the transporter, and therefore, is readily removed. Experiments were carried out in two ways, each yielding similar results. First, cells were preincubated for 24 hours with 100 μM glutamate, then washed and [Glu]$_o$ measured in MEM, or secondly, glutamate was directly applied in MEM and changes in [Glu]$_o$ were monitored.

Figures 10A, 10B:
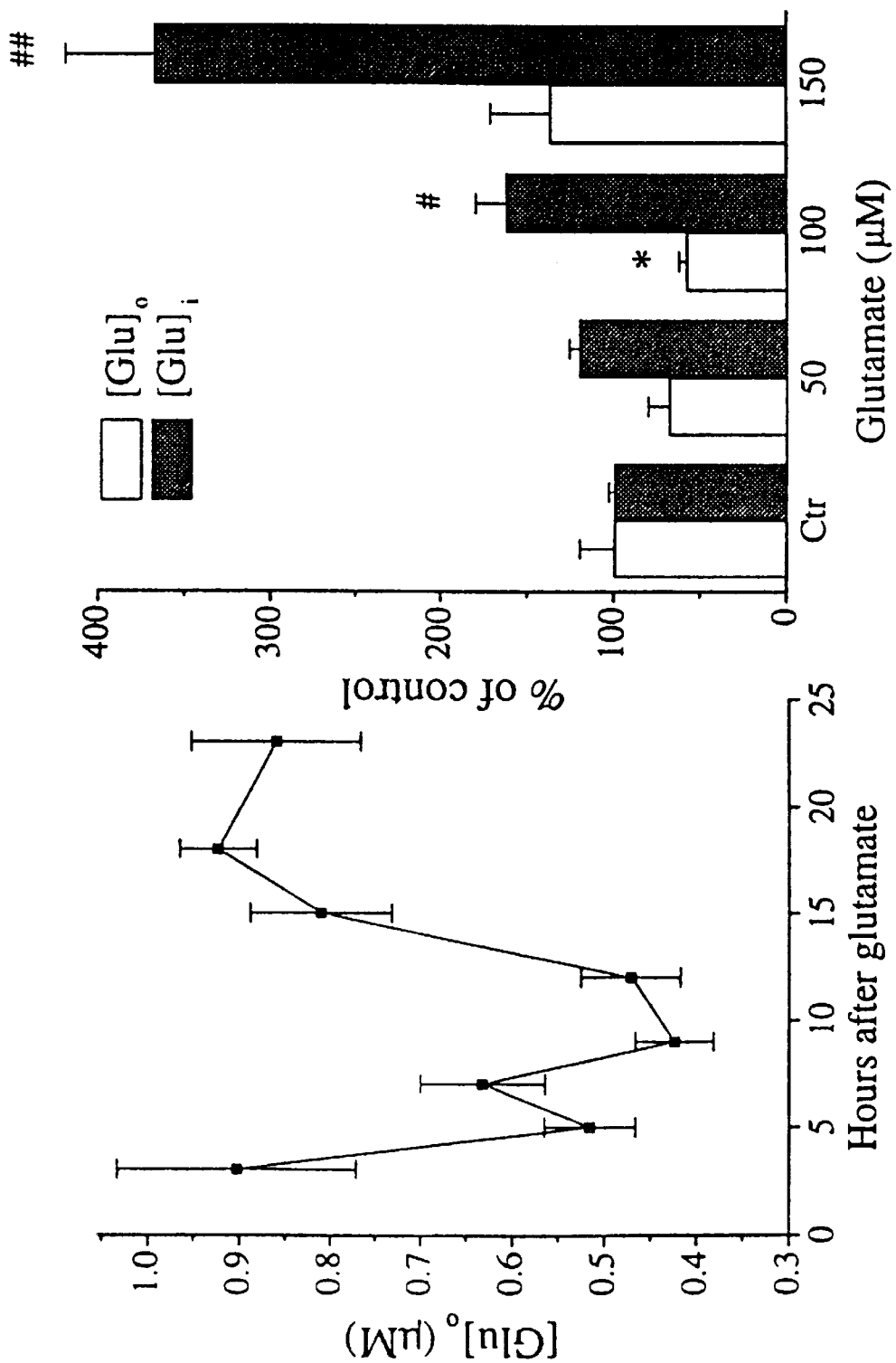
(FIG. 10A). 100 μM glutamate was applied to a hippocampal astrocytes (P22, 28DIV), and [Glu]$_o$ was plotted as a function of time 3 hours after glutamate application. A delayed undershoot in [Glu]$_o$ was observed.
(FIG. 10B). Comparison of [Glu]$_o$ and [Glu]$_i$ in cultures 3.5 hours after treatment with 50–150 μM glutamate. [Glu]$_o$ and [Glu]$_i$ were normalized to % of control. Lower than control [Glu]$_o$ were observed in cultures that received 5014 100 μM glutamate, despite an increase in [Glu]$_i$.
Figure 10C:
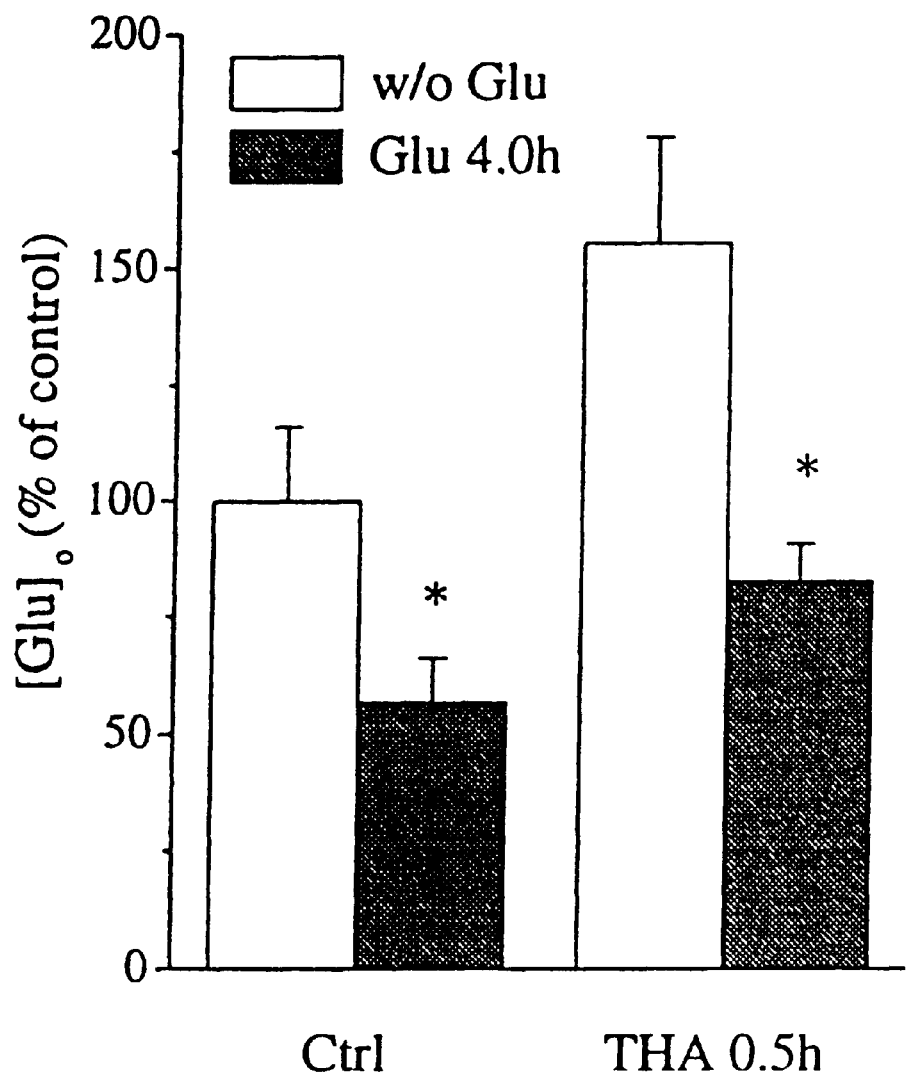
(FIG. 10C). Glutamate induced glutamate undershoot (GIGU) retards THA induced glutamate release. 3.5 hours after application of 100 μM glutamate (n=12), 200 μM THA was applied to 6 wells of each group and compared to untreated controls. [Glu]$_o$ was sampled 30 minutes after THA. (n=6, mean±SE, t-test. *P<0.05 [Glu]$_o$ vs. control; # P<0.05, ## P<0.001 [Glu]$_i$ vs control).

Representative experiments are shown in FIGS. 10A and 10B. A P22 hippocampal astrocyte culture (30DIV) was placed in MEM augmented with 20 mM glucose for 24 hours, and then challenged with 100 μM glutamate. [Glu]$_o$ was then sampled at the indicated time points (FIG. 10A). The initial decline in [Glu]$_o$ was identical to that observed under control conditions. However, [Glu]$_o$ subsequently decreased to levels significantly lower than control (≈0.4 μM, as compared to around 0.9 μM in control). This glutamate "undershoot" was maintained for approximately 10 hours, after which it gradually returned to control levels. This phenomena, which was called "glutamate-induced [Glu]$_o$ undershoot (GIGU)", was observed in the majority of cultures (8 out of 10 experiments, range from P0–P22, >25DIV) that were challenged with 30–100 μM glutamate. The size of the undershoot varied depending on the glutamate concentration applied and as a function of time after glutamate application. Shown in FIG. 10B is a comparison between the intracellular and extracellular glutamate levels 3.5 hours after exposure to different glutamate concentrations ranging from 50–150 μM. For all conditions, there was a dramatic increase of [Glu]$_i$/[Glu]$_o$. Furthermore, it was also observed that during the period of GIGU, application of THA induced less glutamate release from the cultures that received 100 μM glutamate several hours before (FIG. 10C), and these effects were similar to the ACPD effects shown in FIGS. 4A and 4B. Taken together, these data clearly suggest that glutamate per se modulates glutamate transport in a similar manner than ACPD.

EXAMPLE 11
Role Of Glutamate In Parkinson's Disease

Figure 11:
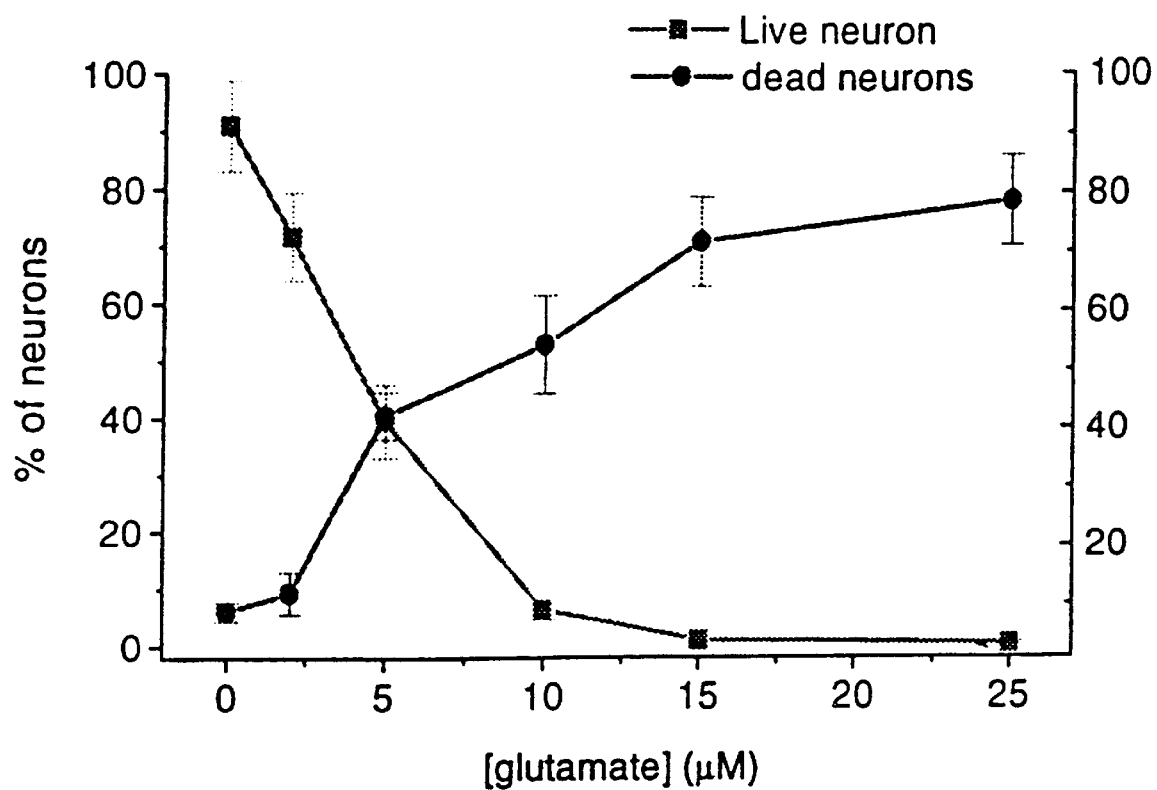
FIG. 11 shows the dose-dependent neuronal death induced by glutamate. IC$_{50}$ values for glutamate induced cell death were close to 5 μM.
Figure 12A:
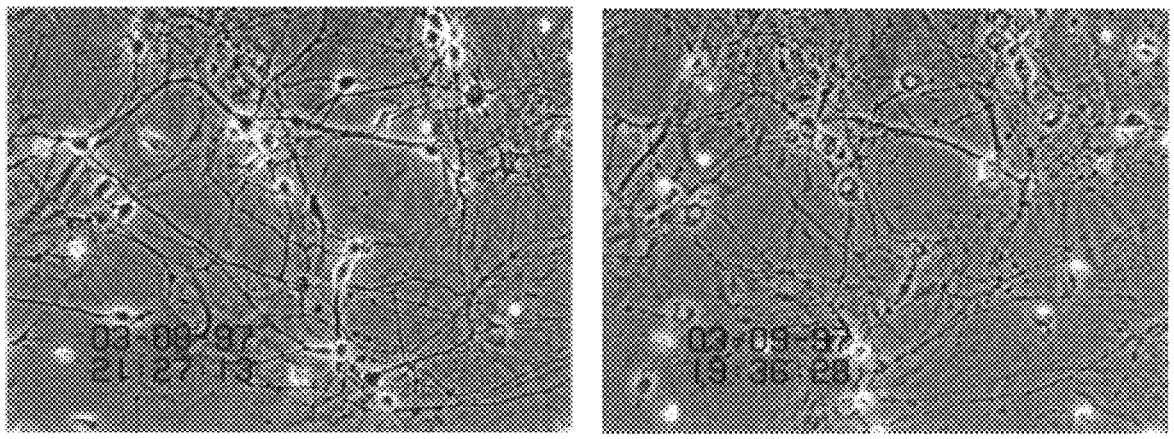
FIG. 12 shows the cell death induced by MPTP or glutamate. Dopaminergic neurons were exposed to 0.2 mM MPTP resulting in wide-spread cell death within less than 24 hours (FIG. 12A). Similarly, exposure to 0.03 mM glutamate was neurotoxic to most neurons (FIG. 12B).
Figure 12B:
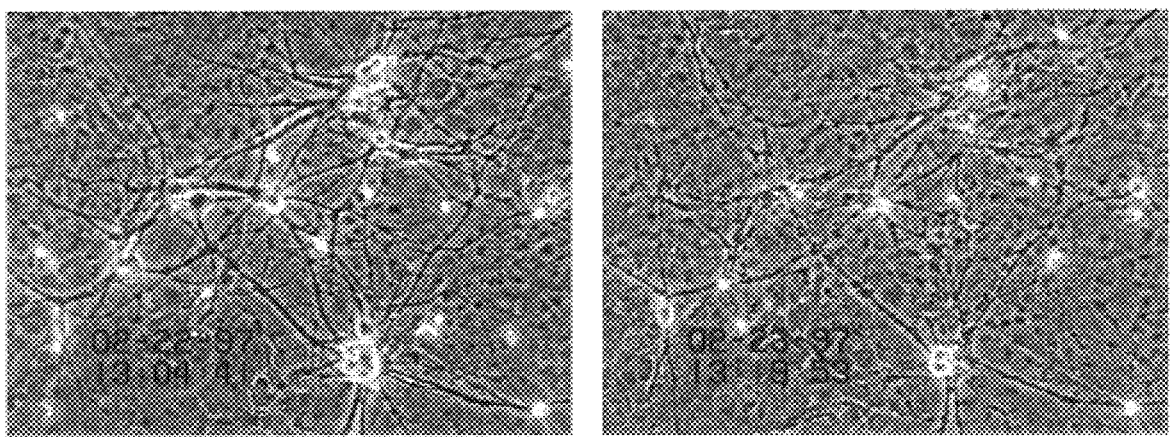
Figure 13:
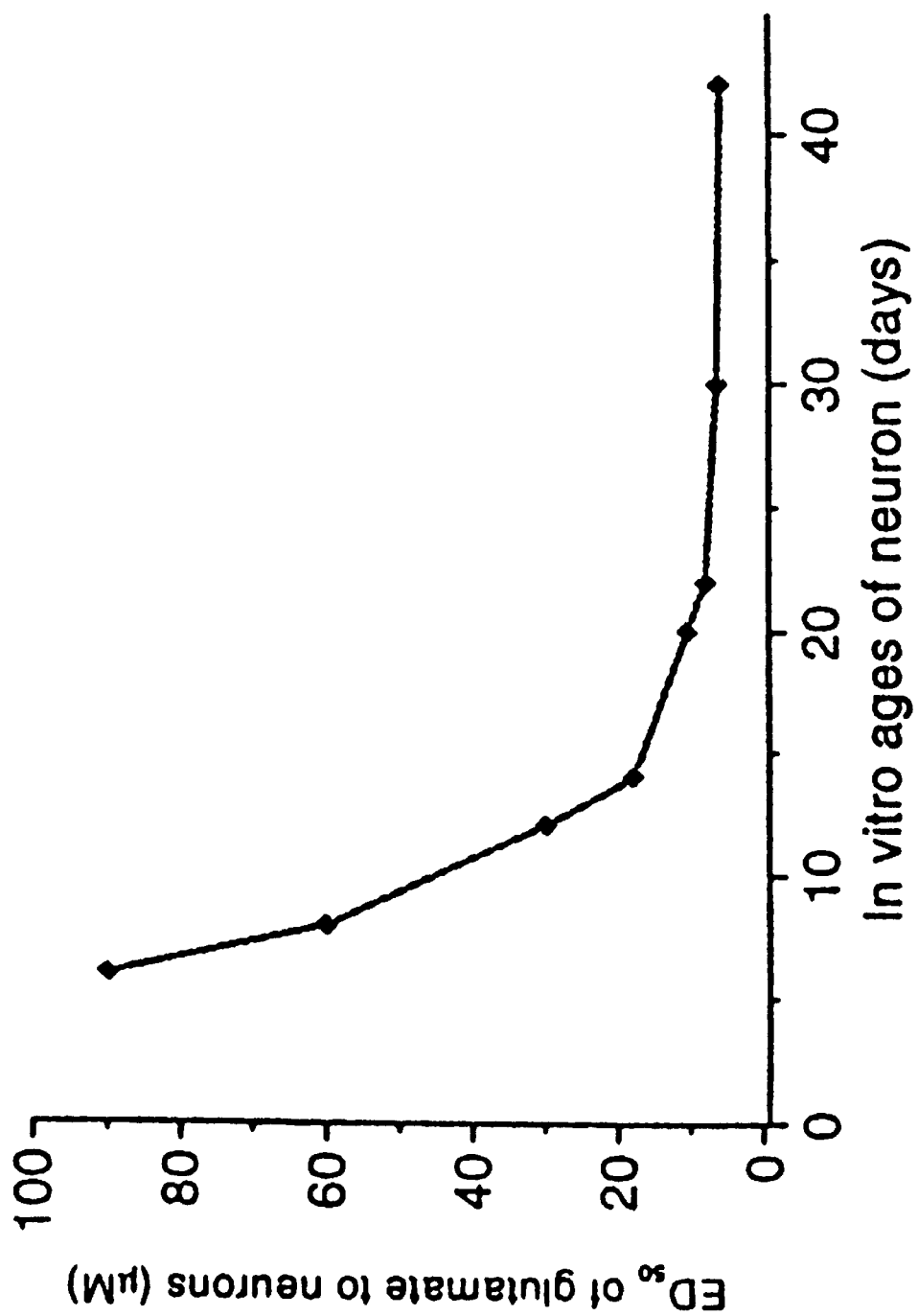
FIG. 13 shows that dopaminergic neurons show an age-dependence in their susceptibility to glutamate neurotoxicity. Only in adult rats, e.g. >30 days, is highest glutamate sensitivity attained.

Cell death of dopaminergic neurons induced by glutamate, and the role of glial glutamate transport in protection of cell death at the cellular level were studied as it relates to Parkinson's disease. Specifically, it was demonstrated that these neurons are highly sensitive to glutamate with an IC$_{50}$ of ≈5 μM. Thus, glutamate concentrations as low as 3–5 μM induced rapid cell death (FIGS. 11 and 12). Glutamate concentrations were also measured in the normal brain. They are typically around 1 μM, below the toxic level for dopaminergic neurons. Interestingly, dopaminergic neurons show an age-dependence in their susceptibility to glutamate. Adult rats (e.g. >30 days) show the highest glutamate sensitivity, whereas young rats are relatively insensitive (FIG. 13). This late onset of glutamate toxicity is compatible with the late onset of Parkinson's disease.

Figure 14:
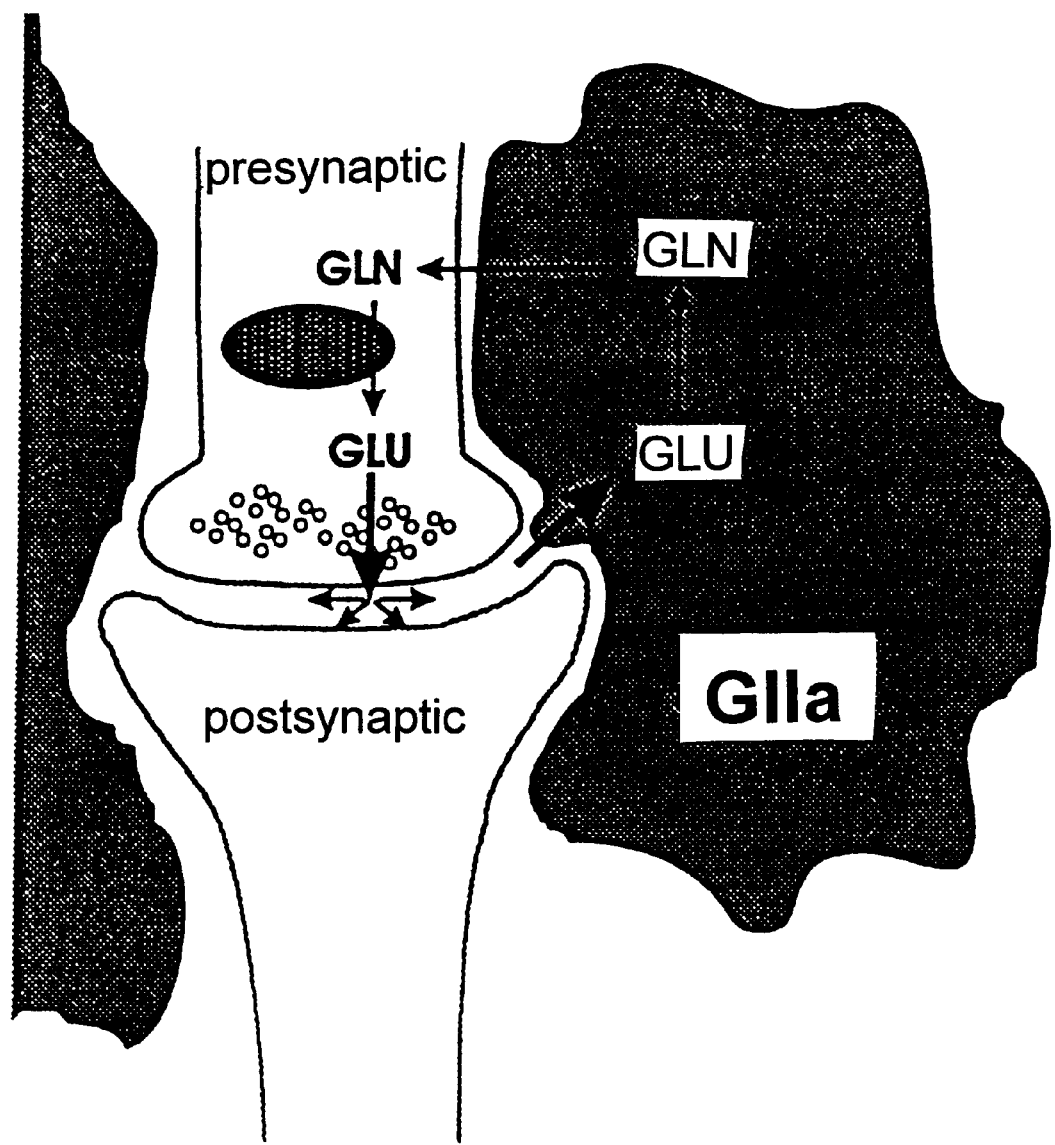
FIG. 14 shows the "detoxification" of extracellular glutamate by glial cells through the Na$^+$-dependent glutamate transporter. Once taken up, glutamate (GLU) is converted to glutamine (GLN) and recycled in neurons for the synthesis of glutamate.
Figure 15:
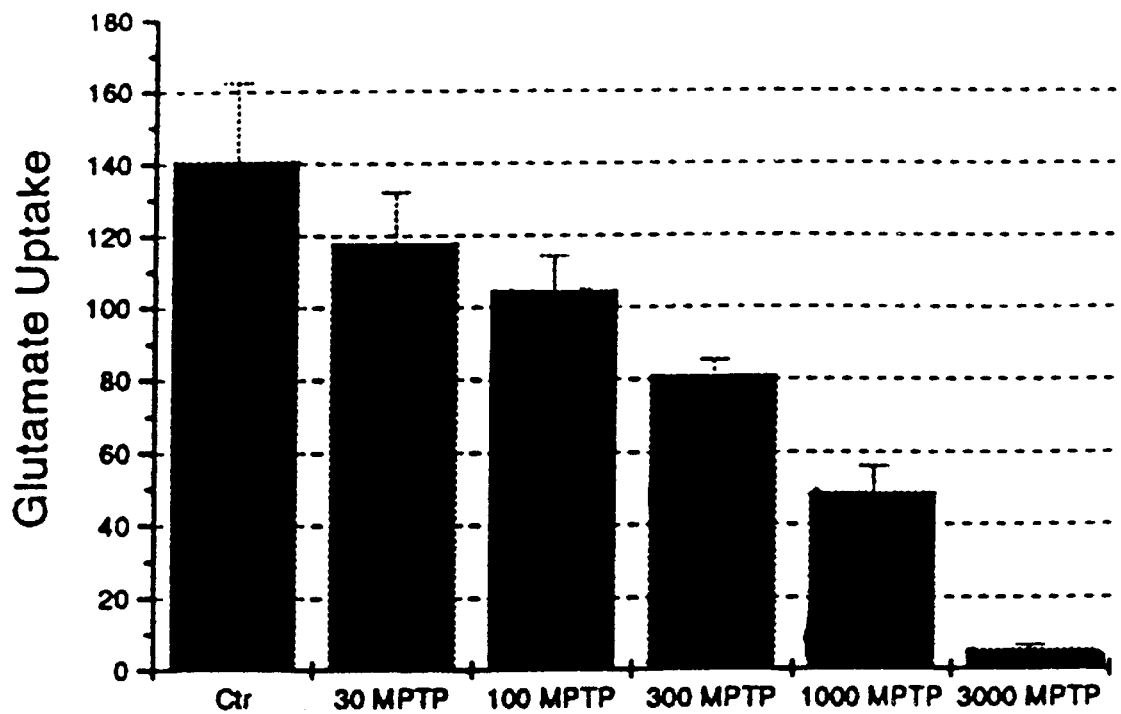
FIG. 15 shows that MPTP inhibits glial glutamate uptake in a dose-dependent manner.
Figure 16:
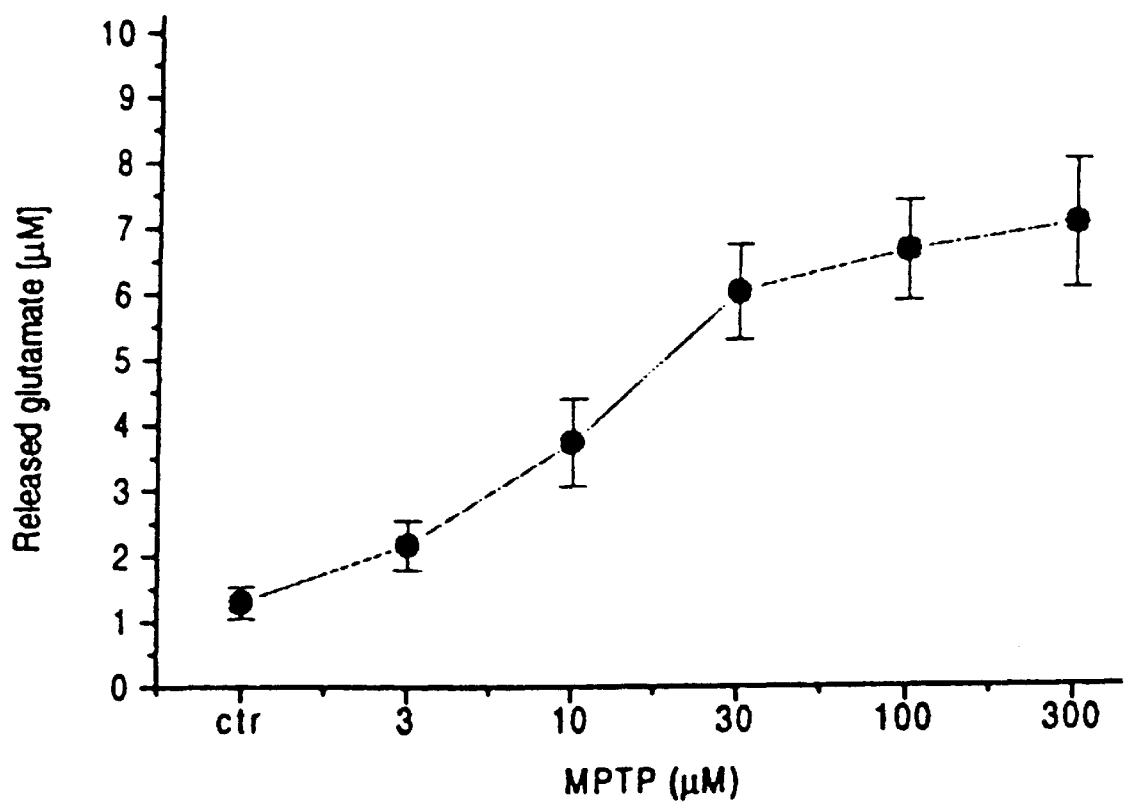
FIG. 16 shows the dose-dependent increase in extracellular glutamate concentrations with exogenous application of MPTP.

The normally low glutamate levels in the brain are established and maintained in glial cells by non-vesicular uptake of glutamate through a Na$^+$-dependent transporter (FIG. 14). Once taken up, glutamate can be converted to glutamine and recycled for neurotransmitter synthesis in neurons (FIG. 14). If glial cells in culture are exposed to high glutamate concentrations (e.g., 100 μM), they will remove it from the extracellular space and essentially "detoxify" the neuronal environment. However, when glial cells are treated with MPTP or MPP$^+$, used to mimic Parkinson's disease in animals, the ability of glial cells to detoxify glutamate is compromised in a dose dependent manner (FIG. 15). Under those conditions, extracellular glutamate levels are elevated to 7 μM (FIG. 16), which is toxic to most surrounding neurons.

Figure 17:
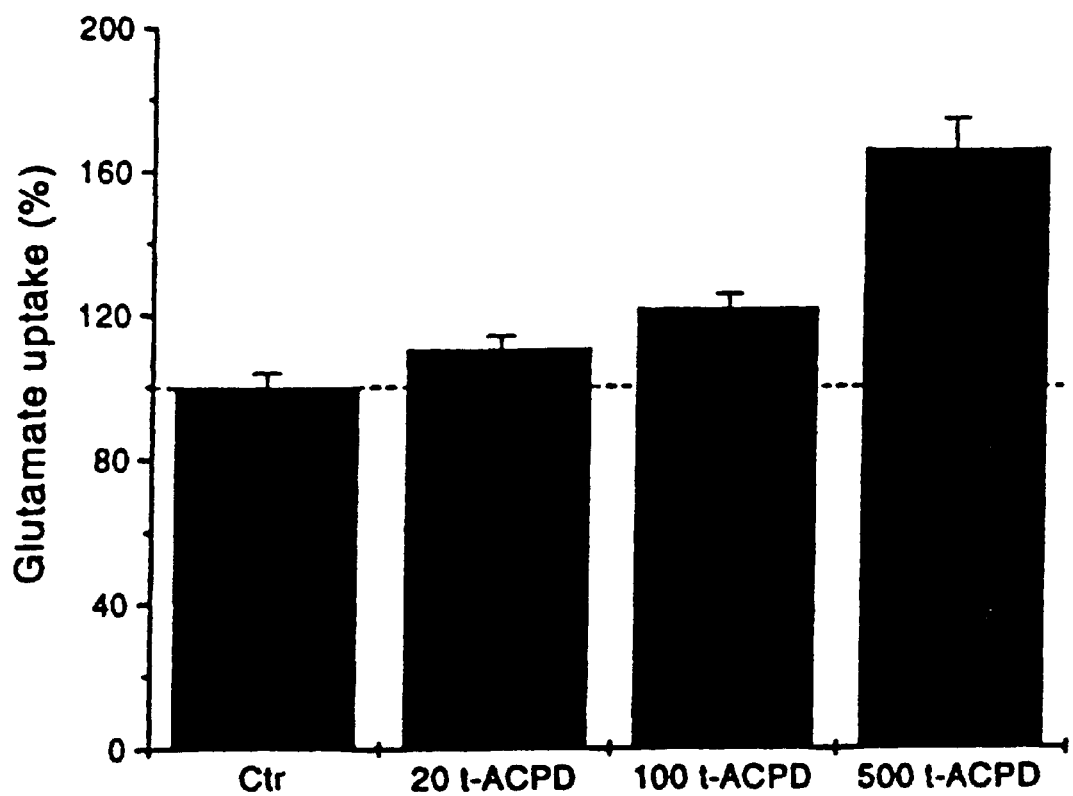
FIG. 17 shows that t-ACPD stimulates glial glutamate uptake in a dose-dependent manner.
Figure 18:
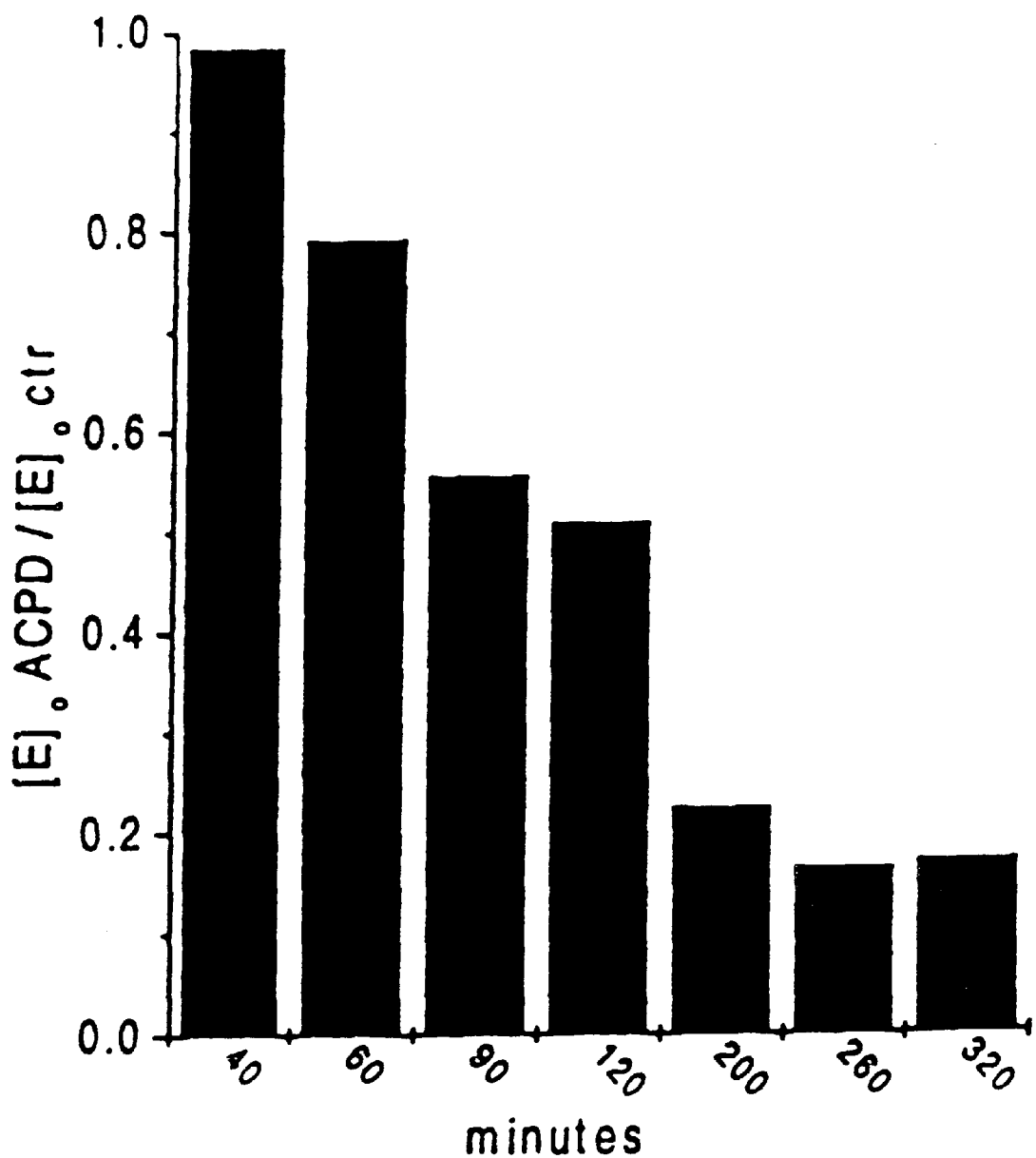
FIG. 18 shows that t-ACPD rectifies glutamate transport in a way that greatly enhances influx over outflow, thus essentially trapping glutamate after uptake.
Figure 19:
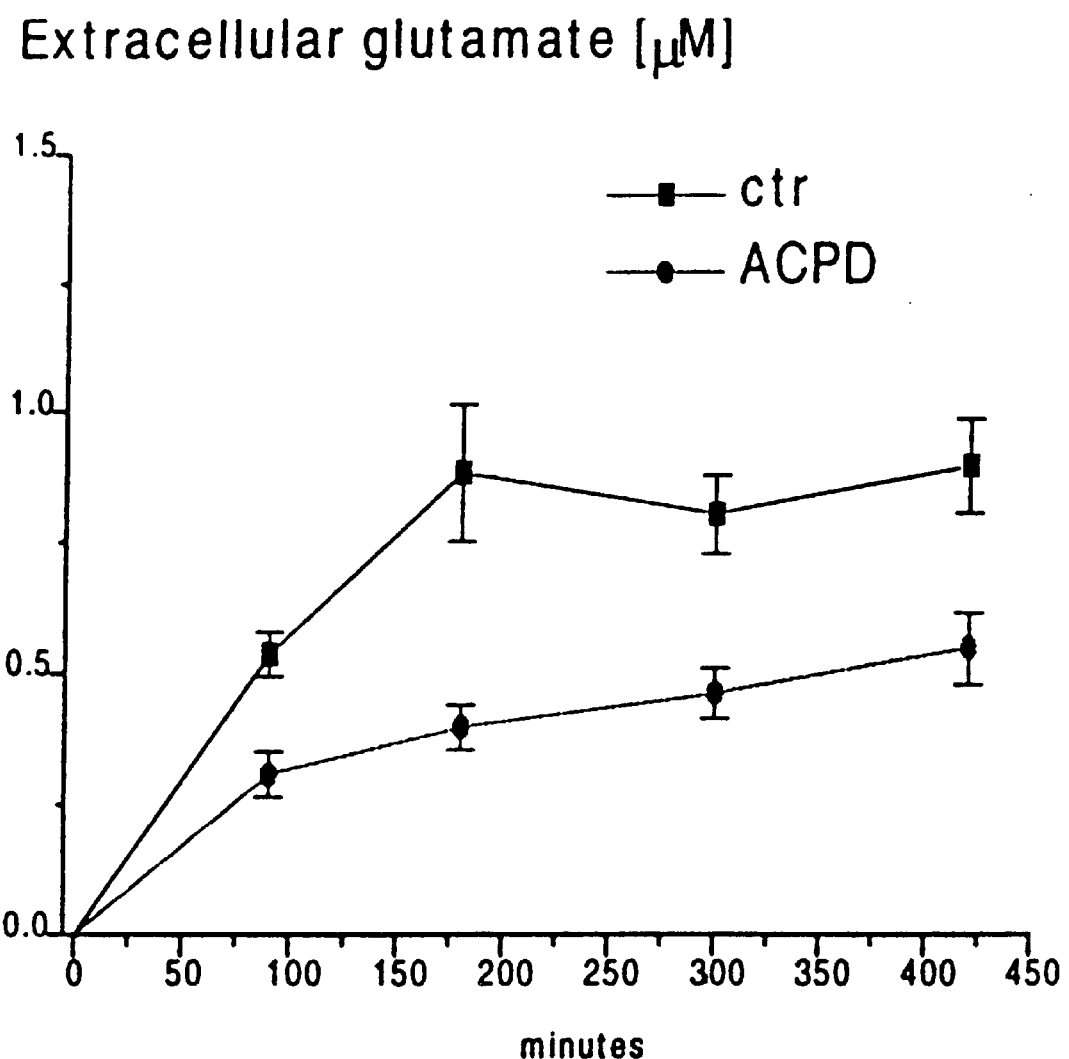
FIG. 19 shows that extracellular glutamate levels are decreased in neuron-glial cocultures after treatment with t-ACPD as compared to controls.

Impaired glial glutamate transport may contribute to the loss of dopaminergic neurons in Parkinson's disease. Thus, stimulation of this pathway would be neuroprotective. A drug and its receptor on glial cells was identified that allows enhanced glutamate detoxification. Specifically, trans-ACPD (trans-1-amino-1,3-cyclopentane dicarboxylic acid) (t-ACPD), a group II metabotropic glutamate receptor agonist, enhanced glial glutamate uptake (FIG. 17). It's actions were 2-fold; (i) it enhanced glutamate uptake by up to 80%, and (ii) it decreased non-specific release of glutamate, effectively trapping glutamate inside glial cells. In fact, the release of glutamate decreased to such a large extent that it almost made the transporter rectify, e.g. allowing only influx and preventing outflow of glutamate (FIG. 18). Consistent with this data, extracellular glutamate levels were reduced by up to 100% after treatment of glial cells with t-ACPD as compared to control (FIG. 19). More importantly, the loss of glutamate uptake induced by MPTP could be compensated for by treatment of glial cells with t-ACPD. Using antibodies and further pharmacological studies, the receptor that is responsible for these effects has been identified as mGluR2/3. A number of drugs have been developed that target this receptor that could be potentially more selective and/or more potent than t-ACPD.

EXAMPLE 12

Additional Evidence of Neuroprotection by t-ACPD

Figure 20:
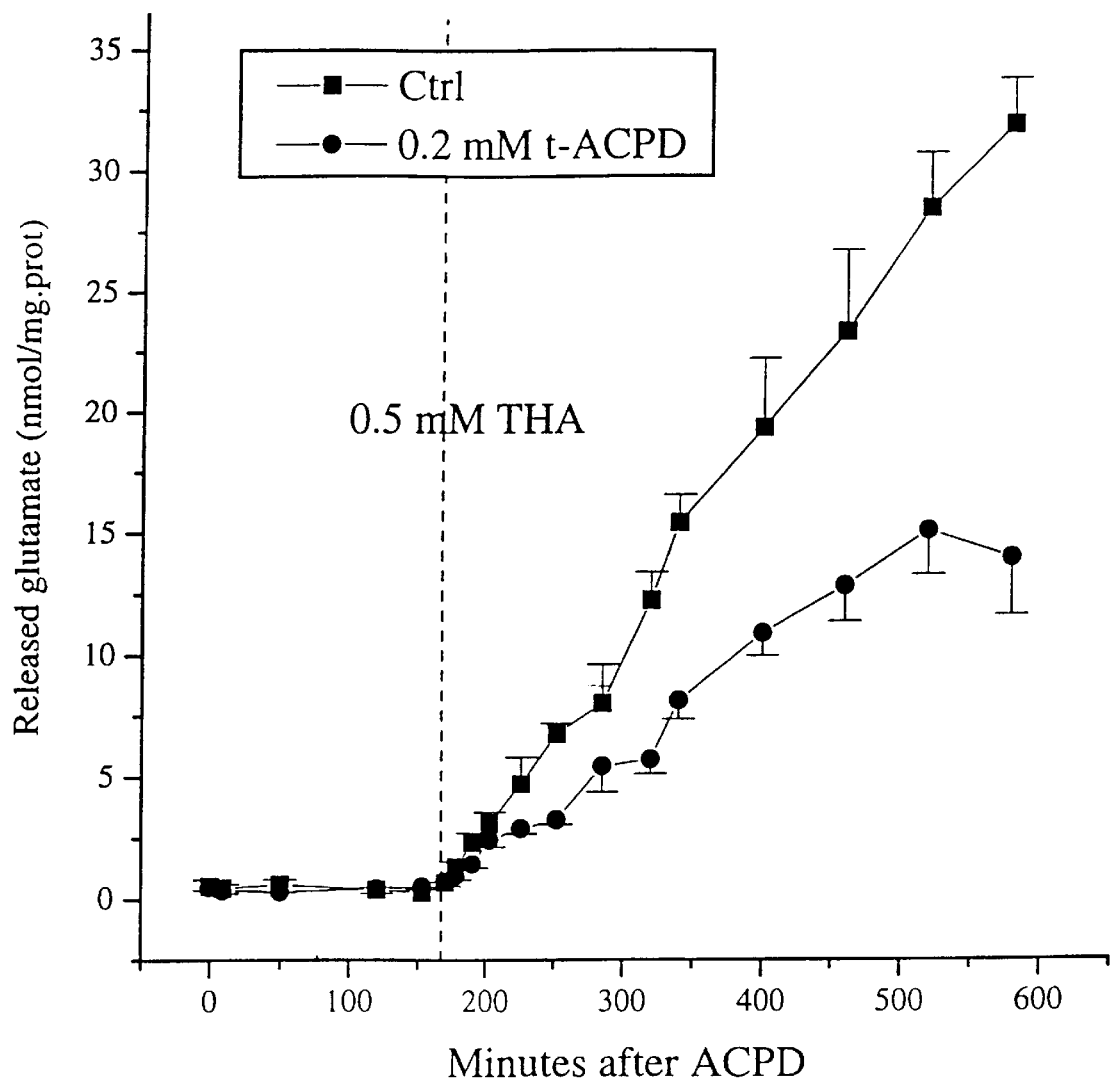
FIG. 20 shows the effect of t-ACPD on glutamate release in rat hippocampal brain slices.

To test the applicability of these results in more intact tissue, acute rate hippocampal brain sections were used to evaluate effects of t-ACPD on glutamate release. This was accomplished using THA, a heteroexchange drug that is also a substrate for the glutamate transporter. For each molecule of THA transported into the cell, one molecule of glutamate is released. Therefore, THA allows the induction of glutamate release. It was determined that variable pretreatments of brain sections with t-ACPD lead to markedly reduced levels of glutamate release from astrocytes as compared to untreated controls (FIG. 20). For example, a 400 min pretreatment reduced THA-induced glutamate release by ≈40%, and much larger effects were observed after a 10 h pretreatment (FIG. 20).

Figure 21A:
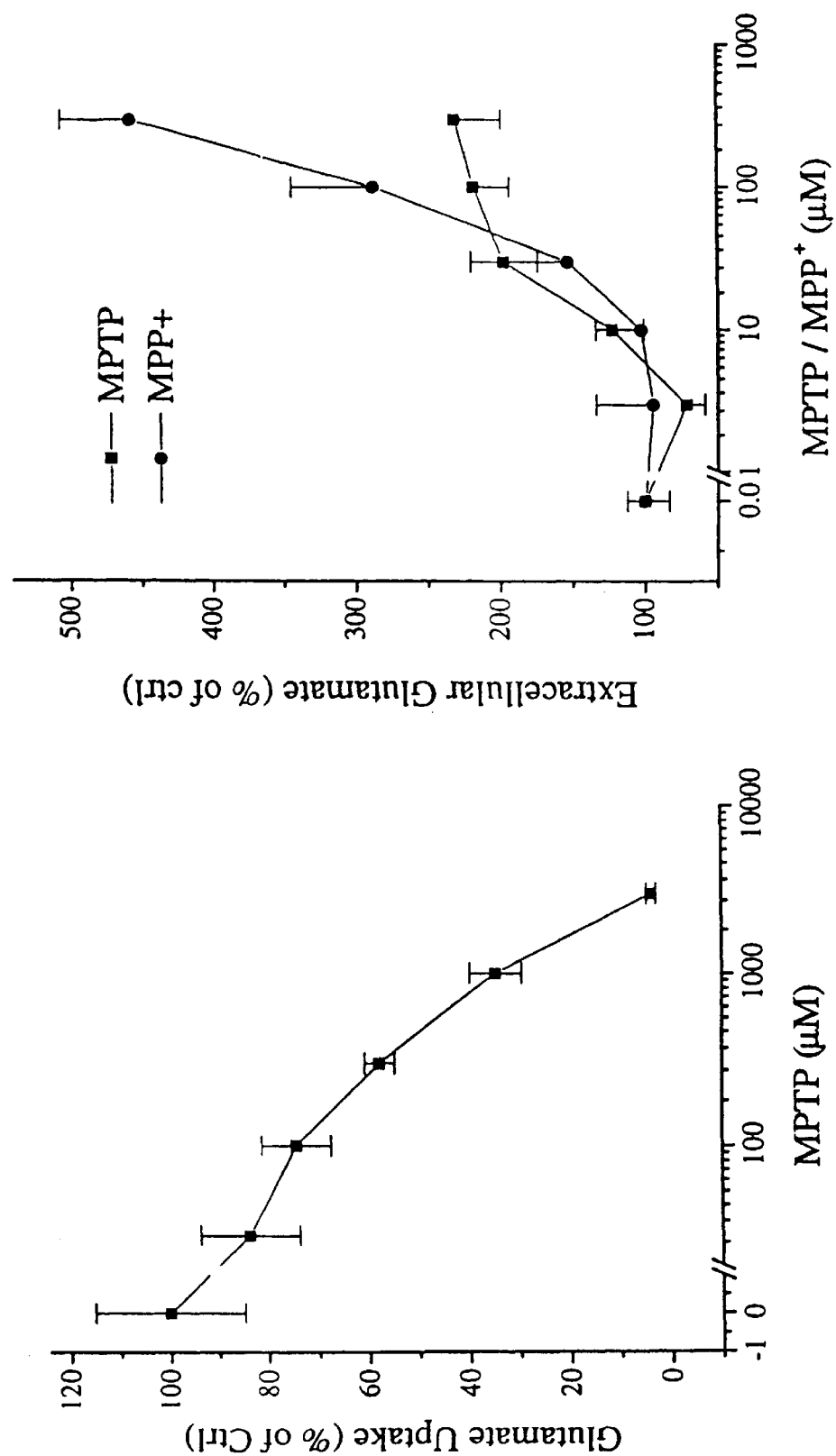
FIG. 21 shows that MPTP impairs astrocytic glutamate uptake and that t-ACPD is able to restore extracellular glutamate levels to normal.
Figure 21B:
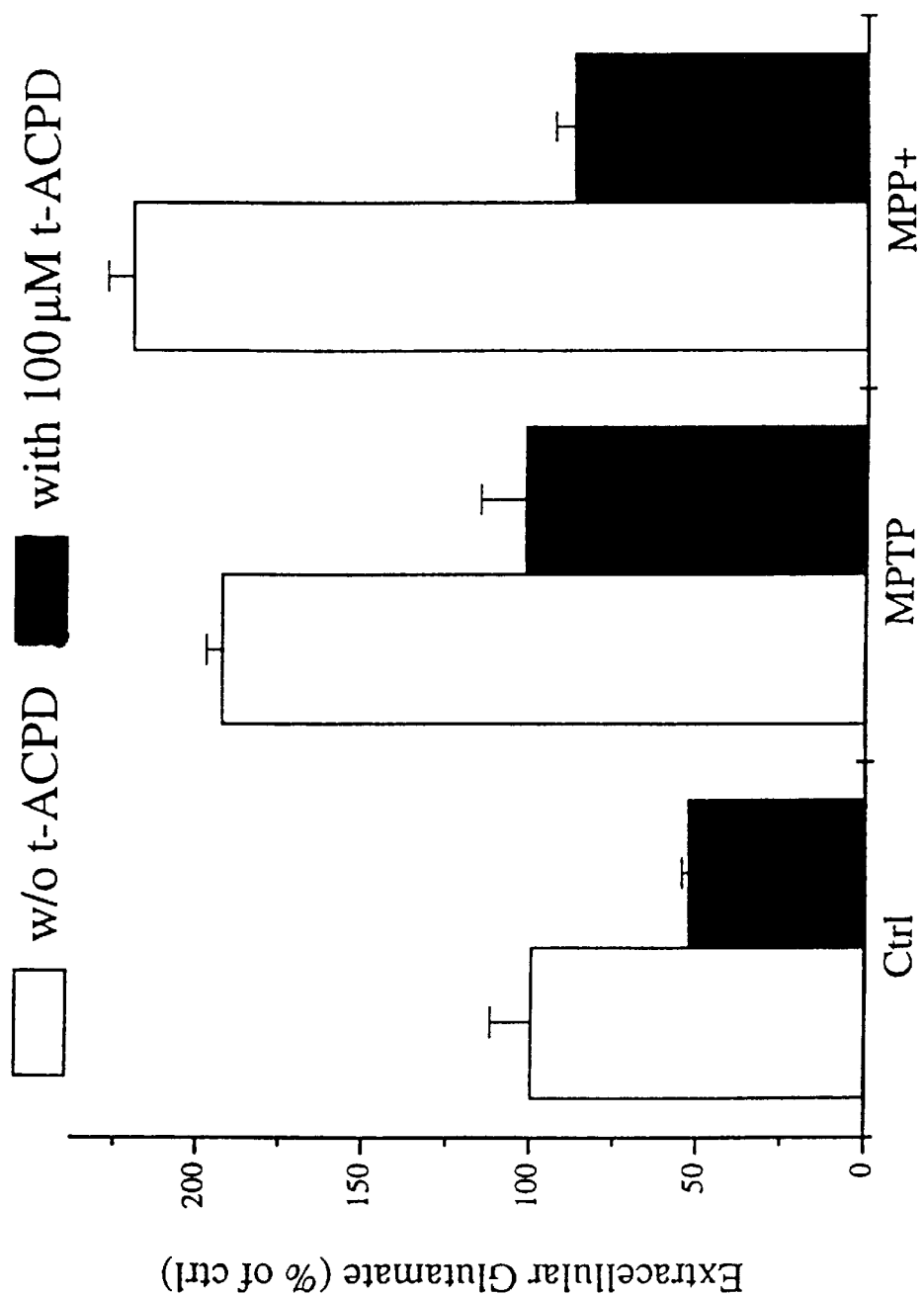

In Parkinson's disease, it is believed that neurons may die of excitotoxic exposure to glutamate. The present invention determined that MPTP directly effects glutamate uptake into astrocytes (FIG. 21, top left). Moreover, exposure of cells to MPTP and particularly the active form, MPP$^+$, resulted in up to 5-fold elevations of extracellular glutamate levels (FIG. 21, top right), sufficient to kill neurons. This increased release may be sufficient to explain some of the subsequent neurodegeneration. This release of glutamate induced by MPP$^+$ can be completely inhibited by t-ACPD (FIG. 21, bottom), providing compelling evidence for its action as a neuroprotectant agent.

Conclusions

The present invention demonstrates the modulation of Na$^+$-dependent glutamate transport in hippocampal astrocytes by activation of mGluR receptors, resulting in long lasting, up to 5-fold attenuation of $[Glu]_o$ concentrations. The pharmacological and immunohistochemical data suggest that these effects were primarily mediated by group II mGluR receptors. These data suggest that astrocytic mGluRs function as sensors to monitor changes in $[Glu]_o$ and adjust the rate of glutamate transport to maintain $[Glu]_o$ at levels that do not cause excitotoxic neural injury.

The immunohistochemical identification of group II mGluR's in hippocampal astrocytes is in agreement with previous studies (Tanabe et al. 1993; Testa et al. 1994; Petralia et al. 1996) suggesting that mGluR2/3 receptors are the most abundant mGluRs in glial cells. The absence of specific antibodies to group III receptor does not allow further immunohistochemical dissection at the present time. However, the use of relatively selective group II agonists strongly argue that the observed effects were mediated by group II receptors.

The most potent agonists were S-4CPG and 1S3R-ACPD. Since ACPD is more frequently used than S-4CPG, most of the experiments were conducted with ACPD. ACPD effects on astrocytes have been previously reported (Porter et al., 1996; Winder et al. 1996), and particularly, changes in Ca$^{++}$ and cAMP level appear to be induced by activation of glial mGluRs. Those authors suggested that mGluRs may function is a receptor that mediates neuronal-glial cross-talk. The present invention describes a "housekeeping" role to the functions of glial mGluRs, namely to modulate astrocytic glutamate transport. Clearly, the natural ligand for mGluRs is glutamate, which not only binds to mGluRs, but is also the substrate for Na$^+$-dependent glutamate transport into astrocytes. The latter function appears to be essential to maintain low $[Glu]_o$, thereby preventing neural injury and ensuring proper synaptic transmissions. It appears intuitive that a sensor for $[Glu]_o$ must exist to allow dynamic modulation of transport rates. The present invention suggests that mGluRs serve as such a sensor and triggers feedback regulation of glutamate transport. In particular, the finding that glutamate itself can mimic ACPD effects supports this notion.

Surprisingly, mGluR modulation of glutamate transport, both by ACPD and glutamate per se, persisted in the absence of the agonists and lasted for many hours. This suggests that the proposed feedback regulation would occur with a rather long time-constant, and may be designed to respond slowly to produce persistent changes in ambient glutamate. It remains to be shown how these changes affect the transporter, however, based on experiments using cycloheximide, ACPD effects did not involve protein synthesis.

Since $[Glu]_o$ is affected by changes in glutamate release from neurons, non-vesicular release from glia, as well as glutamate uptake, the observed reductions in $[Glu]_o$ could have resulted from modulation of any or all of these processes. The majority of the effect can be attributed to a down-regulation of astrocytic glutamate release, with only modest enhancements of uptake. Indeed, at the level of resolution afforded by these assays, it is possible that the modest effects on uptake could have resulted from block of release. Interestingly, reduced release did not result in an accumulation of intracellular glutamate in astrocytes, suggesting that glutamate must have been effectively metabolized. This is consistent with the finding that increases in $[Glu]_i$ modulate the glutamate metabolism inside the astrocytes (McKenna et al. 1996). Furthermore, no significant changes of intracellular glutamate levels were observed after a 24 hours exposure to 1S3R-ACPD (FIG. 4D).

Previous studies in mouse cortical astrocytes (Gegelashvili et al. 1996) suggest that glutamate application leads to changes in the expression of the predominant glial glutamate transporter GLAST. However, these studies failed to see changes in the net rate of astrocytic glutamate transport by trans-ACPD. Unlike the present study, this previous report did not attempt to measure changes in $[Glu]_o$ levels, which is not determined by the rate of uptake alone, but by the balance between uptake and non-vesicular glutamate release (Attwell et al. 1993). Moreover, the present invention detected significant regional heterogeneity with regards to mGluR modulation of glutamate uptake. While significant enhancement of uptake by ACPD in hippocampal and spinal cord astrocytes was observed, such effects in astrocytes cultured from cortex was not observed. The above studies (Gegelashvili et al. 1996) examined cortical astrocytes only and this regional heterogeneity could explain why the effects presented herein had previously gone undetected.

In the normal brain, $[Glu]_o$ is at threshold concentrations for activation of many glutamate receptors, especially NMDA receptors (Patneau et al., 1990; Izumi et al. 1992; Zorumski et al. 1996), L-AP4 sensitive presynaptic mGluRs (Forsythe et al., 1990), and is close to the threshold of Kainate and AMPA receptors (Keinanen et al. 1990; Stein et al. 1992). Small changes in [Glu]$_o$ would thus be expected to influence fast synaptic transmission. It is thus conceivable that even modest changes in astrocytic glutamate transport and non-vesicular release may have long-lasting modulatory effects on such synapses, enhancing or reducing "background noise", which in turn may modulate the activity of neuronal glutamate receptors (Forsythe et al., 1990; Izumi et al. 1992).

The following references were cited herein:

Attwell D, et al. (1993) Neuron 11: 401–407.
Baba A, et al. (1993) Neurosci Lett 149: 182–184.
Benveniste H, et al. (1984) J Neurochem 43: 1369–1374.
Boss V, et al. (1994) Mol Pharmacol 45: 1177–1182.
Boss V, et al. (1995) Neurosci Lett 184: 1–4.
Bruno V, et al. (1997) J Neurosci 17: 1891–1897.
Bushell TJ, et al. (1996) Brit J Pharmacol 117: 1457–1462.
Casabona G, et al. (1992) J Neurochem 59: 1161–1163.
Choi, D. W. (1988a) Neuron 1: 623–634.
Choi, D. W. (1988b) Proceedings, Annual Meeting of the Medical Section of the American Council of Life Insurance 1988: 129–155.
Choi D W, et al. (1990) Ann Rev Neurosci 13: 171–182.
Cholewinski A J, et al. (1989) Neurochem Int 15: 365–369.
Deryugina E I, et al. (1996) J Cell Sci 109: 643–652.
Estin C, et al. (1986) Brain Res Bull 16: 723–731.
Forsythe I D, et al. (1990) J Physiol (Lond) 429: 1–16.
Fosse V M, et al. (1986) J Neurochem 47: 340–349.
Gebicke-Haerter P J, et al. (1994) Neuroche Int 24: 1–12.
Gegelashvili G, et al. (1996) Neuroreport 8: 261–265.
Gegelashvili G, et al. (1997) Mol Pharmacol 52: 6–15.
Genazzani A A, et al. (1993) Brain Res 622: 132–138.
Gilbert S F, et al. (1975) Cell 5: 11–17.
Griffiths R, et al. (1994) Biochem Pharmacol 47: 267–274.
Hertz, L. (1979) Prog. Neurobiol. 13: 277–323.
Hornykiewicz, O. (1966) Pharmacological Reviews 18: 925–964.
Huttenlocher A, et al. (1996) J Cell Biol 134: 1551–1562.
Isaacson J S, et al. (1993) J Neurophysiol 70: 2187–2191.
Izumi Y, et al. (1992) Neurosci Lett 137: 245–248.
Jane D E, et al. (1994) Brit J Pharmacol 112: 809–816.
Jung M, et al. (1996) J .Neurosci 16: 7920–7929.
Kanai Y, et al. (1992) Nature 360: 467–471.
Kawabata S, et al. (1996) Nature 383: 89–92.
Keinanen K, et al. (1990) Science 249: 556–560.
Kemp M C, et al. (1996) Europ J Pharmacol 309: 79–85.
Kimelberg H K, et al. (1989) J Neurosci 9: 1141–1149.
Kimelberg H K, et al. (1990) J Neurosci 10: 1583–1591.
Kimelberg H K, et al. (1988) Glia 1: 219–224.
Langston, J. W., et al. (1983) Science 219: 979–980.
Levi G, et al. (1992) J Neurochem 58: 1943–1952.
Levitt, P., et al. (1982) PNAS USA 79: 6385–6389.
Lindsay R M, et al. (1982) Brain Res 243: 329–343.
Manahan-Vaughan D (1997) J Neurosci 17: 3303–3311.
Masu M, et al. (1991) Nature 349: 760–765.
McKenna M C, et al. (1996) J Neurochem 66: 386–393.
Mennerick S, et al. (1994) Nature 368: 59–62.
Mereu, G., et al. (1991) J. Neurosci. 11: 1359–1366.
Merlin L R, et al. (1995) J Neurophysiol 74: 896–900.
Miller S, et al. (1995) J Neurosci 15: 6103–6109.
Nicholls D, et al. (1990) Trends Pharmacol Sci 11: 462–468.
Nicklas, W. J., et al. (1985) Life Sciences 36: 2503–2508.
Nicoletti F, et al. (1996) Trends Neurosci 19: 267–271.
Ogata T, et al. (1992) J Neurochem 58: 1957–1959.
Ottersen O P (1989) Anat & Embryol 180: 1–15.
Patneau D K, et al. (1990) J Neurosci 10: 2385–2399.
Petralia R S, et al. (1996, Neurosci 71: 949–976.
Pin J P, et al. (1995) Neuropharmacology 34: 1–26.
Pines G, et al. (1992) Nature 360: 464–467.
Porter J T, et al. (1995) Glia 13: 101–112.
Porter J T, et al. (1996) J Neurosci 16: 5073–5081.
Prezeau L, et al. (1994) Mol Pharmacol 45: 570–577.
Ransom, B. R., et al. (1987) J. Neurosci. Lett. 75: 323–328.
Rothstein J D, et al. (1996) Neuron 16: 675–686.
Rutledge E M, et al. (1996) J Neurosci 16: 7803–7811.
Schoepp D D, et al. (1993) Trends Pharmacol Sci 14: 13–20.
Sheng et al. (1997) Nature 386: 221–222.
Snyder, S. H. et al. (1986) Neurology 36: 250–258.
Stein E, et al. (1992) Mol Pharmacol 42: 864–871.
Storck T, et al. (1992) PNAS USA 89: 10955–10959.
Swanson R A, et al. (1997) J Neurosci 17: 932–940.
Szatkowski M, et al. (1990) Nature 348: 443–446.
Tanabe Y, et al. (1993) J Neurosci 13: 1372–1378.
Testa C M, et al. (1994) In: Conn PJ, Patel J eds), pp 99–123. Totowa, N. J.: Humana Press Inc.
Velasco I, et al. (1996) J Neurosci Res 44: 551–561.
Volterra A, et al. (1996) Europ J Neurosci 8: 2019–2028.
Walz, W. Prog. Neurobiol. 33: 309–333, 1989.
Winder D G, et al. (1996) J Physiol (Lond) 494: 743–755.
Winder D G, et al. (1995) J Neurochem 64: 592–599.
Winder D G, et al. (1996) J Neurosci Res 46: 131–137.
Ye ZC, et al. (1996) Neuroreport 7: 2181–2185.
Zorumski C F, et al. (1996) J Physiol (Lond) 494: 465–477.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of treating an individual having a pathophysiological state characterized by an increased level of extracellular glutamate, comprising the step of administering to said individual a therapeutically effective dose of a metabotropic glutamate receptor agonist, wherein pathophysiological state is selected from the group consisting of head or spinal cord trauma, stroke and epilepsy.

2. The method of claim 1, wherein said treatment results in a reduction in neuronal extracellular levels of glutamate.

3. The method of claim 1, wherein said agonist is selected from the group consisting of trans-1-aminocyclopentane-1,3-dicarboxylic acid, (1S,3R)-1-aminocyclopentane-1,3-dicarboxylic acid, (S)-4-carboxyphenylglycine, (1R, 3S)-1-aminocyclopentane-1,3-dicarboxylic acid, L-CCG-I and L-cystein-sulfinic acid.

4. The method of claim 1, wherein said agonist is trans-1-aminocyclopentane-1,3-dicarboxylic acid.

5. The method of claim 4, wherein said trans-1-aminocyclopentane-1,3-dicarboxylic acid is administered to said individual in an amount of from about 0.5 mg/kg to about 80 mg/kg.

6. The method of claim 1, wherein said agonist is (1S, 3R)-1-aminocyclopentane-1,3-dicarboxylic acid.

7. The method of claim 6, wherein said (1S,3R)-1-aminocyclopentane-1,3-dicarboxylic acid is administered to said individual in an amount of from about 0.5 mg/kg to about 80 mg/kg.

8. The method of claim 1, wherein said metabotropic glutamine receptor agonist decreases non-specific release of glutamate by glial cells.

9. The method of claim 1, wherein said individual has a neuronal injury which results in increased levels of extra-cellular glutamate.

* * * * *

UNITED STATES PATENT AND TRADEMARK OFFICE
CERTIFICATE OF CORRECTION

PATENT NO.   : 6,013,672
DATED        : January 11, 2000
INVENTOR(S)  : Zu-Cheng Ye and Harald W. Sontheimer It is certified that error appears in the above-identified patent and that said Letters Patent is hereby corrected as shown below:

<u>Column 1,</u>
Line 7, "P50 HD32901" should read -- P50 HD32904 --.

Signed and Sealed this

Nineteenth Day of November, 2002

Attest:

Attesting Officer

JAMES E. ROGAN
Director of the United States Patent and Trademark Office